(12) United States Patent
Fisher et al.

(10) Patent No.: US 8,673,931 B2
(45) Date of Patent: Mar. 18, 2014

(54) BICYCLIC HETEROCYCLIC SPIRO COMPOUNDS

(76) Inventors: Abraham Fisher, Holon (IL); Nira Bar-Ner, Rishon Letzion (IL); Victoria Nachum, Rishon Letzion (IL)

(*) Notice: Subject to any disclaimer, the term of this patent is extended or adjusted under 35 U.S.C. 154(b) by 93 days.

(21) Appl. No.: 13/146,209

(22) PCT Filed: Jan. 26, 2010

(86) PCT No.: PCT/IL2010/000064
§ 371 (c)(1),
(2), (4) Date: Jul. 26, 2011

(87) PCT Pub. No.: WO2010/084499
PCT Pub. Date: Jul. 29, 2010

(65) Prior Publication Data
US 2011/0281903 A1  Nov. 17, 2011

Related U.S. Application Data

(60) Provisional application No. 61/147,143, filed on Jan. 26, 2009.

(51) Int. Cl.
| | | |
|---|---|---|
| A61K 31/438 | (2006.01) | |
| A61P 3/10 | (2006.01) | |
| A61P 25/28 | (2006.01) | |
| C07D 491/20 | (2006.01) | |
| C07D 493/10 | (2006.01) | |
| C07D 495/10 | (2006.01) | |
| C07D 498/10 | (2006.01) | |
| C07D 513/10 | (2006.01) | |

(52) U.S. Cl.
USPC ............... 514/278; 546/16; 546/17; 546/19

(58) Field of Classification Search
None
See application file for complete search history.

(56) References Cited

U.S. PATENT DOCUMENTS

| | | | |
|---|---|---|---|
| 3,481,942 A | 12/1969 | Loev | |
| 4,855,290 A | 8/1989 | Fisher et al. | |
| 4,876,260 A | 10/1989 | Fisher et al. | |
| 4,900,830 A | 2/1990 | Fisher et al. | |
| 4,981,858 A | 1/1991 | Fisher et al. | |
| 5,053,412 A | 10/1991 | Fisher et al. | |
| 5,221,675 A | 6/1993 | Chung et al. | |
| 5,407,938 A | 4/1995 | Fisher et al. | |
| 5,534,520 A | 7/1996 | Fisher et al. | |
| 5,852,029 A | 12/1998 | Fisher et al. | |
| 7,049,321 B2 | 5/2006 | Fisher et al. | |
| 7,349,251 B2 | 3/2008 | Tempel | |

FOREIGN PATENT DOCUMENTS

| | | |
|---|---|---|
| EP | 0189370 A2 | 7/1986 |
| EP | 0205247 A2 | 12/1986 |
| EP | 0303391 A2 | 2/1989 |
| EP | 0311313 A2 | 4/1989 |
| EP | 0337547 A2 | 10/1989 |
| EP | 0350118 A2 | 1/1990 |
| EP | 0452101 A2 | 10/1991 |
| JP | 63208590 A | 8/1988 |
| JP | 02164882 A | 6/1990 |
| WO | 90/15804 A1 | 12/1990 |
| WO | 95/03303 A1 | 2/1995 |
| WO | 03/092580 A1 | 11/2003 |

OTHER PUBLICATIONS

Tsukamoto et. al., Chem. Pharm. Bull. 1995, 43, 842-852.
Fisher, Jap. J. Pharmacol. 2000, 84: 101-12.
Fisher, Neurotherapeutics, 5: 433-42, 2008.
Maillard et al., Chimica Therapeutica, vol. 6, No. 4, 1971, pp. 257-261.
Kametani et al., Chem & Pharm Bull 1970, 18(6) 1161.
Ager et al., J Pharm Sci 1969, 58(4) 499.
CAS Registry Nos. 1026890-94-7, 1010934-47-0, 951996-61-5, 951977-71-2, 951965-19-8, 951954-41-9, 951944-56-2, 951928-66-8, 942833-24-1.
Saunders et al., J. Med. Chem., vol. 31, No. 2, 1988, pp. 486-491.

Primary Examiner — Janet L Andres
Assistant Examiner — Timothy R. Rozof
(74) Attorney, Agent, or Firm — Daniel Feigelson

(57) ABSTRACT

There are disclosed bicyclic heterocyclic spiro compounds; pharmaceutical compositions comprising these compounds; and methods for the treatment in a mammal of diseases and conditions which are susceptible to modulation of the M1 muscarinic receptor, including Alzheimer's disease, insulin resistance syndrome and type 2 diabetes. Other embodiments are also disclosed.

20 Claims, 2 Drawing Sheets

BICYCLIC HETEROCYCLIC SPIRO COMPOUNDS

RELATED CASES

This is a 35 U.S.C. §371 application of PCT/IL2010/000064, filed Jan. 26, 2010, and claims the benefit under 35 U.S.C. §120 of said PCT application, and further claims the benefit under 35 U.S.C. §119(e) of U.S. Provisional Application No. 61/147,143, filed Jan. 26, 2009. The contents of this provisional application are incorporated herein by reference.

FIELD OF THE INVENTION

The invention relates to bicyclic heterocyclic Spiro compounds which are ligands for G-protein coupled receptors (GPCRs), and in particular function as muscarinic receptor agonists, to pharmaceutical compositions comprising these compounds, and to methods for the treatment of Alzheimer's disease, insulin resistance syndrome and type 2 diabetes in a mammal.

BACKGROUND

A wide spectrum of diseases with unmet medical need share some common pathogenesis that may be treatable, in principle, with protein kinase C (PKC) activators and Glycogen synthase kinase-3β (GSK-3β), inhibitors, respectively. Three such disease states, Alzheimer's disease (AD) (a neurological central nervous (CNS) disease), and Insulin resistance syndrome (IRS) and type-2 diabetes (T2D) (two metabolic diseases which are related to each other), are described briefly below. There is a close connection between IRS/T2D and AD (Sima and Li, Rev. Diabetic Stud. 2006, 3:161-168).

AD is a degenerative brain disorder characterized clinically by progressive loss of memory, by synaptic loss, by the presence of neuritic plaques consisting of β-amyloid (Aβ) by the presence of neurofibrillary tangles (NFT), and by loss of cholinergic neurons in the basal forebrain. Aβ are neurotoxic peptides. Tau ($\tau$) are microtubule-associated proteins necessary for neurite outgrowth. Hyperphosphorylated tau proteins are in fact toxic and are the principal component of paired helical filaments (PHF) and NFTs. Insulin resistance induces chronic peripheral insulin elevations, reduces insulin activity, and reduces brain insulin levels. IRS and associated conditions such as T2D and hypertension are associated with age-related memory impairment and AD (Sima and Li, Rev Diabetic Stud 2006, 3:161-168).

A number of kinases are involved in AD pathology and IRS/T2D. Thus the amount of protein kinase C (PKC) is decreased in the brains of people suffering from AD, and this decrease has been shown to be correlated with neuropathological staging. This emphasizes the importance of this kinase as a major therapeutic target in AD (Kurumatani et al Brain Res 1998; 796:209-21).

Another kinase, GSK-3β, plays an important regulatory role in a multitude of cellular processes, ranging from cell membrane-to-nucleus signaling, gene transcription, translation, cytoskeletal organization to cell cycle progression and survival (Eldar-Finkelman, Trends Molec Med. 2002, 8:126-32; Bhat et al., Neurosignals 2002, 11:251-61; Balaram et al., Cell Mol Life Sci 2006, 63:1226-35). GSK-3β has been linked to most of the primary abnormalities associated with AD such as AD tau hyperphosphorylation, Aβ-induced neurotoxicity and presenilin-1 (PS-1) mutation pathogenic effects. Active GSK-3β triggers signal transduction events that participate in cell death, indicating that part of AD pathology could result from abnormal GSK-3β expression and activity. Furthermore, inactivation of GSK-3β has been correlated with decreased Aβ secretion (Sun et al., Neurosci. Lett. 2002, 321:61-4). Presently it is hypothesized that GSK-3β is the missing link between the β-amyloid and tau-pathology, placing GSK-3β as prominent player in the pathogenesis in AD [Takashima, J Alzheimers Dis 2006, 9 (3 Suppl), 309-17].

GSK-3β phosphorylates glycogen synthase and regulates the glucose metabolism pathway. Thus GSK-3β is a central negative regulator in the insulin signaling pathway, and it may have a role in insulin resistance (Gasparini et al. Trends Pharmacol Sci 2002:23:288-92; Janssens et al. Investig New Drugs 2006; 24: 263-80).

Thus inhibition of GSK-3β may mimic the action of certain hormones and growth factors, such as insulin, which use the GSK-3β pathway. This strategy may permit the bypassing of a defective receptor (e.g. the insulin receptor), or another faulty component of the signaling machinery, so that the biological signal will take effect even when some upstream players of the signaling cascade are at fault, such as in non-insulin-dependent type 2 diabetes [Tanabe et al, PLoS Biol. 2008 (2): e37; Wagman et al, Curr Pharm Design, 2004, 10:1105-1137].

Treatment strategies for the diseases mentioned above may include PKC activators and GSK-3β inhibitors. This can be achieved in principle either via indirect (GPCR-mediated) or direct modulation of these kinases. In case of direct activators of PKC or inhibitors of GSK3β, the quest is for highly potent and selective ligands. However, such therapeutic strategies would not be free of adverse effects as their target kinases are involved in a plethora of processes and downstream cascades. Thus direct targeting of these kinases for their function in one pathway (and linked disease) will alter their function in another pathway and potentially give rise to serious side effects (off-target side effects).

Therefore the ideal therapy for compounds that directly target these kinases should modulate selectively the discrete pathway(s) involved in the disease state. Such kinases can be modulated from outside the cell membrane via GPCRs. GPCRs convert signals received from outside the cell into biological processes inside the cell via signal transduction pathways. Such signal transduction pathways modulated by GPCRs are elegant systems by which cells and organisms can amplify subtle signals to generate robust responses. This downstream amplification process allows for clinical development of partial agonists that have a moderate binding potency and do not cause desensitization of the GPCR-mediated signaling following prolonged treatment in chronic disease states such as AD, IRS and T2D.

It is desirable for drug candidates for GPCR-modulation to have selectivity for the target GPCR subtype in order to prevent activation of other GPCR subtypes. A subclass of GPCRs are the muscarinic receptors (mAChR). Five genetically distinct human muscarinic receptors designated M1-M5 have been cloned (Buckley et al. Mol. Pharmacol. 1989; 35: 469-76; Hulme et al. Ann Rev Pharmacol Toxicol 1990; 30: 633-73). M1 mAChR, prevalent in the cortex, hippocampus and striatum, has an important role in cognitive processing and in particular in short-term memory, which is impaired in AD. M1 selective muscarinic agonists may serve as an anti-dementia drug treatment. The therapeutic potential of such compounds should, in principle, be less affected than the cholinesterase inhibitors (AChE-Is) by the extent of degeneration of presynaptic cholinergic terminals, and thus may represent a more rational treatment for AD than the FDA-approved AChE-Is (Review: Fisher, Neurotherapeutics, 5:

433-42, 2008). A number of bicylic Spiro-compounds, some reported to be M1-selective agonists, have been disclosed (U.S. Pats. Nos. 4,855,290, 4,981,858, 4,900,830, 4,876,260, 5,053,412, 5,407,938, 5,534,520, 5,852,029, 7,049,321, 5,221,675, 7,349,251).

A relation between three of the major hallmarks characteristic of AD has been reported: the CNS cholinergic hypofunction, formation of Aβ peptide amyloid plaques and tangles containing hyperphosphorylated tau proteins. In this context, vicious cycles link the cholinergic hypofunction in AD with Aβ peptide and tau phosphorylation. Stimulation of M1 mAChRs can increase cleavage of amyloid precursor protein (APP) in the middle of its β-amyloid region. This cleavage produces the secreted, neurotrophic and neuroprotective APPs (α-APPs), preventing the formation of Aβ peptide. M1 agonists may be of value in preventing Aβ formation by selectively promoting the α-secretase processing pathway in AD. Furthemore, stimulation of M1 mAChRs can decrease tau hyperphosphorylation (Review: Fisher, Neurotherapeutics 5:433-42, 2008). Thus some of the GPCR subtypes, and in particular the M1 mAChR, are involved in modulation of a multitude of functions, both in health and disease. PKC can be activated by several GPCRs including, but not limited to, M1 mAChR, metabotropic receptors and Wnt signaling (Farias et al., Neurobiol. Dis. 2004, 47:337-48; Mudher et al., J. Neurosci. 2001, 21:4987-95; Ballou et al., J. Biol. Chem. 2001, 44: 40910-916).

GPCRs in general can contain more than one site. In this context, the mAChR subtypes contain both orthosteric (primary binding site of the natural neurotransmitter, acetylcholine) and allosteric sites (may or may not alter the orthosteric site and the effects acetycholine).

Many of the pathological features of CNS and PNS diseases including AD and IRS/T2D, respectively, involve oxidative stress-related features. An oxidative stress in AD caused by Aβ can propagate a chain of events and vicious cycles leading to a blockade of some GPCR-induced signal transduction (best documented for M1 mAChR) and further accumulation of neurotoxic Aβ. Antioxidants can, in principle, prevent such vicious cycles (Fisher, Jap. J. Pharmacol. 2000, 84: 101-12; Kelly et al., Proc. Nat'l Acad. Sci. USA 1996 93:6753-58).

Oxidative stress can ultimately lead to both the onset and subsequent complications of T2D. Although antioxidant treatments can show benefits in animal models of diabetes, new and more powerful antioxidants are needed to demonstrate whether antioxidants can be effective in treating complications. Furthermore, it appears that oxidative stress is only one factor contributing to diabetic complications; thus, antioxidant treatment would likely be more effective if it were coupled with other treatments for diabetic complications. In particular, novel pathways that involve metabotropic receptor signaling (e.g. GPCR-mediated signaling), and GSK-3β, may be involved in diabetes and would need to be addressed in a comprehensive therapeutic strategy (Maiese et al, Curr Med. Chem. 2007 14:1729-38. Review).

BRIEF DESCRIPTION OF THE INVENTION

There is provided, in accordance with embodiments of the invention, a Spiro compound of formula I:

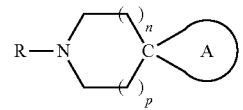

wherein A is selected from the group consisting of

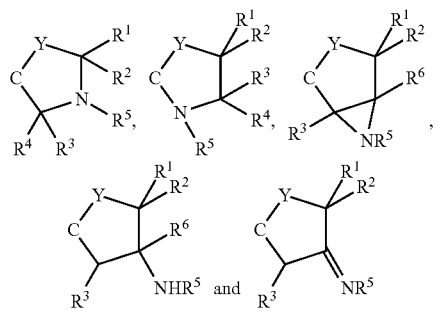

wherein
in all structures the carbon indicated by "C" denotes the Spiro carbon,
R is selected from the group consisting of H and optionally substituted $C_{1-6}$ alkyl,
n and p are each independently selected from 0, 1, 2 and 3, provided that n+p=1, 2 or 3;
Y is —O— or —S—;
$R^2$, $R^3$, $R^4$, and $R^6$ are each independently selected at each occurrence from H, optionally substituted $C_{1-6}$ alkyl, optionally substituted $C_{1-6}$ alkoxy, optionally substituted $C_{1-6}$ hydroxyalkyl, optionally substituted $C_{2-6}$ alkenyl, and optionally substituted phenyl;
$R^5$ is selected from optionally substituted $C_{1-4}$ alkyl, optionally substituted $C_{1-6}$ hydroxyalkyl, optionally substituted $C_{2-6}$ alkenyl, optionally substituted $C_{2-6}$ alkynyl, optionally substituted phenyl, optionally substituted —($C_{1-6}$)alkylindole, optionally substituted heteroaryl, optionally substituted $C_{1-6}$ alkyl heteroaryl, optionally substituted $C_{3-7}$ cycloalkyl, —C(=O)—$R^8$, —$SO_2$—$R^9$, and, when A is

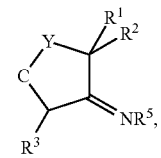

—CO—C(=O)—$R^8$;
$R_2$ is selected from optionally substituted $C_{1-7}$ alkyl, optionally substituted $C_{1-7}$ alkoxy, optionally substituted $C_{2-7}$ hydroxyalkyl, optionally substituted $C_{2-7}$ alkenyl, optionally substituted $C_{2-7}$ alkynyl, optionally substituted $C_{3-7}$ cycloalkyl, optionally substituted aryl, optionally substituted —($C_{1-6}$)alkylindole, optionally substituted —$C_{2-3}$ alkenylindole, optionally substituted —($C_{1-6}$)alkoxyindole, optionally substituted —($C_{1-6}$)alkylindolizine, optionally substituted —$C_{2-3}$ alkenylindolizine, optionally substituted —($C_{1-6}$) alkoxyindolizine, optionally substituted —($C_{1-6}$)alicylisoindole, optionally substituted —$C_{2-3}$alkenylisoindole, optionally substituted —($C_{1-6}$)alkoxyisoindole, optionally substituted —($C_{1-6}$)alkylindaziole, optionally substituted —C$_{2-3}$ alkenylindazole, optionally substituted —(C$_{1-6}$) alkoxyindazole, optionally substituted —(C$_{1-6}$)alkylbenzimidazole, optionally substituted —C$_{2-3}$ alkenylbenzimidazole, and optionally substituted —(C$_{1-6}$) alkoxybenzimidazole; and R$_9$ is aryl substituted by one or more members of the group consisting of alkyl, halogen, nitro, amino, hydroxyl, and CF$_3$, or a pharmaceutically acceptable salt thereof.

In some embodiments of the invention, R is methyl. In some embodiments of the invention, p and n are each 1.

In some embodiments of the invention, A is

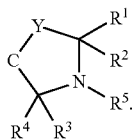

In some embodiments, A is

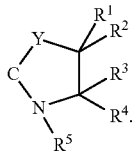

In some embodiments, A is

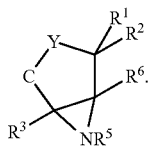

In some embodiments, A is

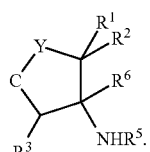

In some embodiments, A is

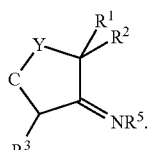

In some embodiments of the invention, R$^1$ is methyl. In some embodiments, R$^1$ is methyl and R$^2$ is H. In some embodiments R$^1$ is methyl and R$^2$, R$^3$ and R$^4$ are each H.

In some embodiments R$^6$ is H.

In some embodiments of the invention, Y is S. In some embodiments Y is O.

In some embodiments R$^5$ is —C(O)—(C$_{1-3}$)-indol-3-yl. In some embodiments R$^5$ is —C(O)—CH$_2$-indol-3-yl. In some embodiments R$^5$ is —C(O)—CH$_2$CH$_2$-indol-3-yl. In some embodiments R$^5$ is —C(O)—CH$_2$CH$_2$-((1-methyl)-indol-3-yl. In some embodiments R$^5$ is —C(O)—CH$_2$CH$_2$CH$_2$-indol-3-yl. In some embodiments R$^5$ is trans —C(O)—CH═CH-indol-3-yl. In some embodiments R$^5$ is —SO$_2$-4-fluorophenyl. In some embodiments R$^5$ is —C(O)CH(n-propyl)$_2$. In some embodiments R$^5$ is —C(O)-(4-hydroxy-3,5-di-tertbutylphenyl). In some embodiments R$^5$ is —C(O)—CH$_2$CH$_3$. In some embodiments R$^5$ is —C(O)—CH(NH$_2$)—CH$_2$-indol-3-yl. In some embodiments A is

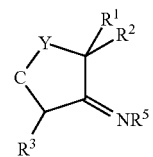

and R$^5$ is —O—C(═O)—CH$_2$CH$_2$-indol-3-yl.

In some embodiments of the invention, the compound is selected from one of the following:

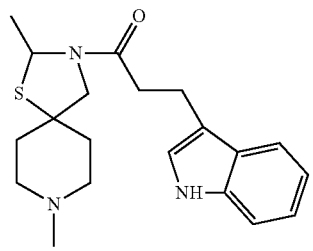

(1-(2,8-dimethyl-1-thia-3,8-diazaspiro[4.5]dec-3-yl)-3-(1H-indol-3-yl)propan-1-one),

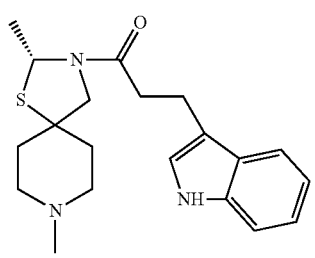 [SMILES: C[C@H]1SC2(CCN(C)CC2)CN1C(=O)CCc1c[nH]c2ccccc12]

((R)-1-(2,8-dimethyl-1-thia-3,8-diazaspiro[4.5]dec-3-yl)-3-(1H-indol-3-yl)propan-1-one),

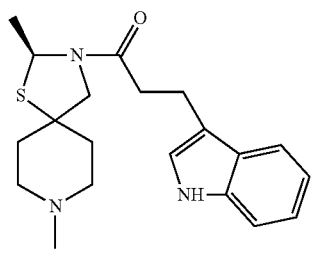

((S)-1-(2,8-dimethyl-1-thia-3,8-diazaspiro[4.5]dec-3-yl)-3-(1H-indol-3-yl)propan-1-one),

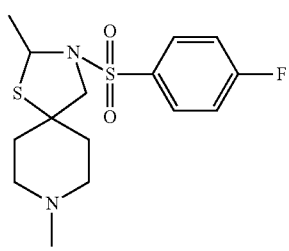 [SMILES: CC1SC2(CCN(C)CC2)CN1S(=O)(=O)c1ccc(F)cc1]

(3-(4-fluorobenzenesulfonyl)-2,8-dimethyl-1-thia-3,8-diazaspiro[4.5]-decane),

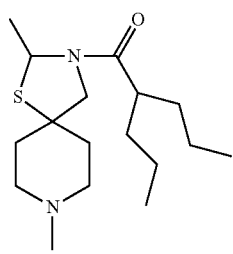 [SMILES: CCCC(CCC)C(=O)N1CC2(CCN(C)CC2)SC1C]

(1-(2,8-dimethyl-1-thia-3,8-diazaspiro[4.5]dec-3-yl)-2-propylpentan-1-one),

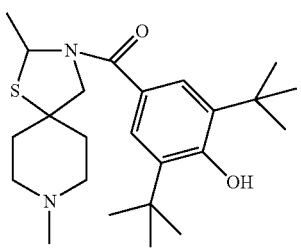 [SMILES: CC1SC2(CCN(C)CC2)CN1C(=O)c1cc(C(C)(C)C)c(O)c(C(C)(C)C)c1]

((3,5-di-tert-butyl-4-hydroxy-phenyl)-(2,8-dimethyl-1-thia-3,8-diaza-spiro[4.5]dec-3-yl)-methanone),

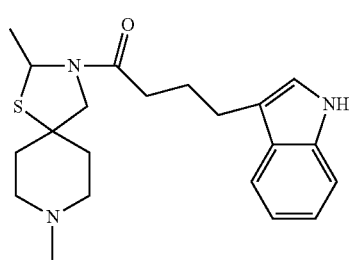 [SMILES: CC1SC2(CCN(C)CC2)CN1C(=O)CCCc1c[nH]c2ccccc12]

(1-(2,8-dimethyl-1-thia-3,8-diazaspiro[4.5]dec-3-yl)-4-(1H-indol-3-yl)butan-1-one),

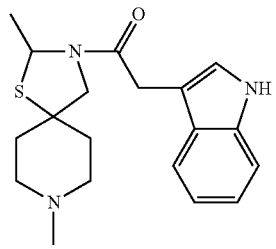 [SMILES: CC1SC2(CCN(C)CC2)CN1C(=O)Cc1c[nH]c2ccccc12]

(1-(2,8-dimethyl-1-thia-3,8-diazaspiro[4.5]dec-3-yl)-2-(1H-indol-3-yl)ethan-1-one),

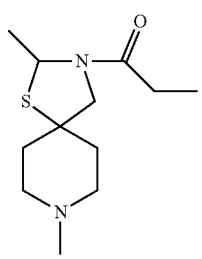 [SMILES: CCC(=O)N1CC2(CCN(C)CC2)SC1C]

(1-(2,8-dimethyl-1-thia-3,8-diazaspiro[4.5]dec-3-yl)-propan-1-one),

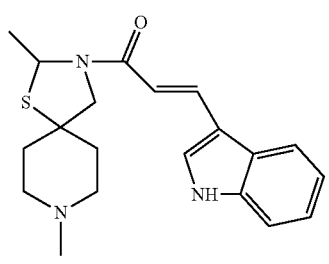 [SMILES: CC1SC2(CCN(C)CC2)CN1C(=O)/C=C/c1c[nH]c2ccccc12]

(1-(2,8-dimethyl-1-thia-3,8-diazaspiro[4.5]dec-3-yl)-3-(1H-indol-3-yl)prop-2-ene-1-one),

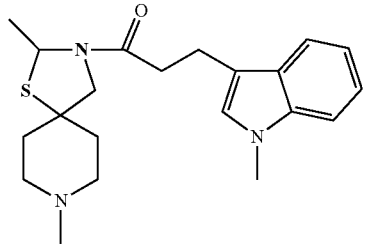 [SMILES: CC1SC2(CCN(C)CC2)CN1C(=O)CCc1cn(C)c2ccccc12]

1-(2,8-Dimethyl-1-thia-3,8-diazaspiro[4.5]dec-3-yl)-3-(1-methyl-indol-3-yl)propan-1-one,

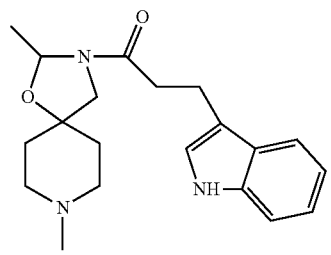 [SMILES: CC1OC2(CCN(C)CC2)CN1C(=O)CCc1c[nH]c2ccccc12]

1-(2,8-dimethyl-1-oxa-3,8-diazaspiro[4.5]dec-3-yl)-3-(1H-indol-3-yl)-propan-1-one,

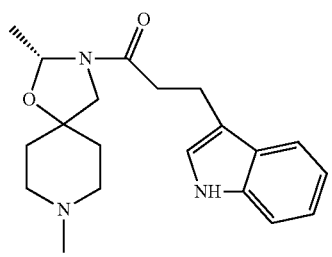 [SMILES: C[C@H]1OC2(CCN(C)CC2)CN1C(=O)CCc1c[nH]c2ccccc12]

((R)-1-(2,8-dimethyl-1-oxa-3,8-diazaspiro[4.5]dec-3-yl)-3-(1H-indol-3-yl)-propan-1-one),

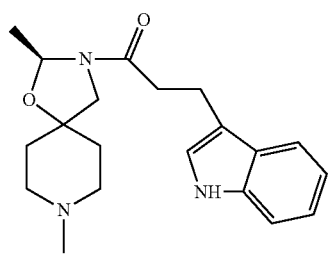 [SMILES: C[C@@H]1OC2(CCN(C)CC2)CN1C(=O)CCc1c[nH]c2ccccc12]

((S)-1-(2,8-dimethyl-1-oxa-3,8-diazaspiro[4.5]dec-3-yl)-3-(1H-indol-3-yl)-propan-1-one)

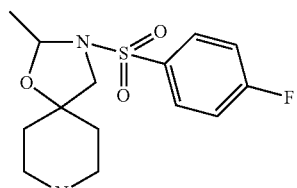

(3-(4-fluorobenzenesulfonyl)-2,8-dimethyl-1-oxa-3,8-diazaspiro[4.5]-decane),

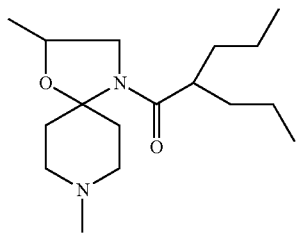 [SMILES: CCCC(CCC)C(=O)N1CC(C)OC12CCN(C)CC2]

(1-(2,8-dimethyl-1-oxa-4,8-diazaspiro[4.5]dec-4-yl)-3-(1H-indol-3-yl)-propan-1-one),

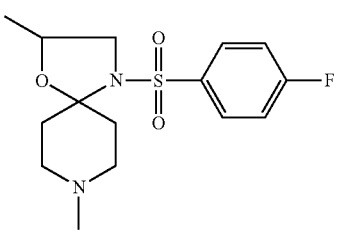 [SMILES: CC1CN(S(=O)(=O)c2ccc(F)cc2)C2(CCN(C)CC2)O1]

(1-(2,8-dimethyl-1-oxa-4,8-diazaspiro[4.5]dec-4-yl)-2-propyl-pentan-1-one),

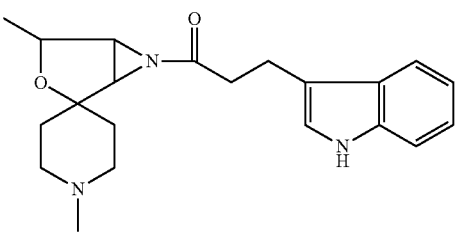 [SMILES: CC1OC2(CCN(C)CC2)C2C1N2C(=O)CCc1c[nH]c2ccccc12]

(4-(4-fluoro-benzenesulfonyl)-2,8-dimethyl-1-oxa-4,8-diaza-spiro[4.5]-decane), (1-(2,8-dimethyl-1-oxa-3,8-diaza-spiro[4.5]dec-3-yl)-2-propyl-pentan-1-one), (1',4-dimethyl-6-(3-indolpropionyl)-spiro-(3-oxa-6-aza-bicyclo[3.1.0]-hexane-2,4'-piperidine)), and

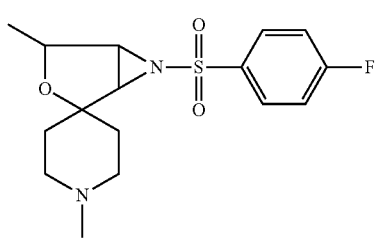 [SMILES: CC1OC2(CCN(C)CC2)C2C1N2S(=O)(=O)c1ccc(F)cc1]

(1',4-dimethyl-6-[3-(4-fluorobenzenesulfonyl)]-spiro-(3-oxa-6-aza-bicyclo[3.1.0]hexane-2,4'-piperidine)),

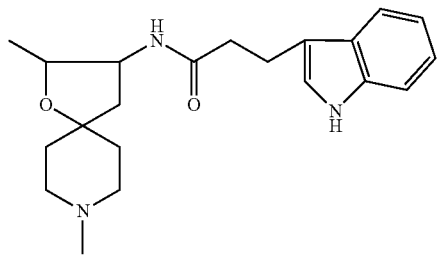 [SMILES: CC1OC2(CCN(C)CC2)CC1NC(=O)CCc1c[nH]c2ccccc12]

N-(2,8-dimethyl-1-oxa-8-aza-spiro[4.5]dec-3-yl)-3-(1H-indol-3-yl)-propionamide,

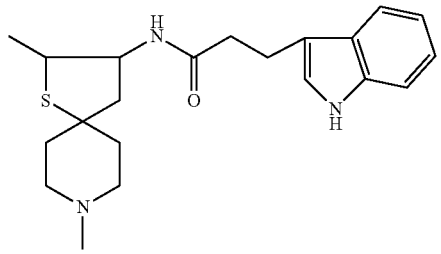 [SMILES: CC1SC2(CCN(C)CC2)CC1NC(=O)CCc1c[nH]c2ccccc12]

N-(2,8-Dimethyl-1-thia-8-aza-spiro[4.5]dec-3-yl)-3-(1H-indol-3-yl)-propionamide,

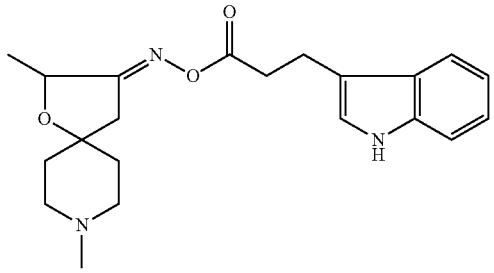 [SMILES: CC1OC2(CCN(C)CC2)C/C1=N\OC(=O)CCc1c[nH]c2ccccc12]

(3E)-2,8-dimethyl-1-oxa-8-azaspiro[4.5]decan-3-one-O—[3-(1H-indol-3-yl)propanoyl]oxime,

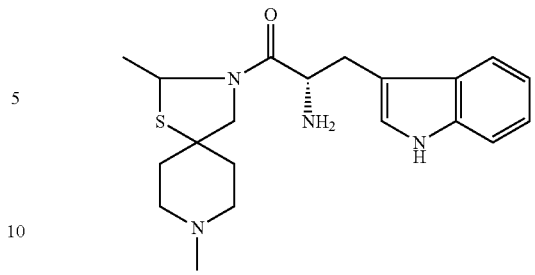

(D)-2-Amino-1-(2,8-dimethyl-1-thia-3,8-diaza-spiro[4.5]dec-3-yl)-3-(1H-indol-3-yl)-propan-1-one or a pharmaceutically acceptable salt thereof.

There is also provided, in accordance with some embodiments of the invention, a compound selected from the group consisting of (1-(2,8-dimethyl-1-thia-3,8-diazaspiro[4.5]dec-3-yl)-3-(1H-indol-3-yl)propan-1-one), (+)-(1-(2,8-dimethyl-1-thia-3,8-diazaspiro[4.5]dec-3-yl)-3-(1H-indol-3-yl)propan-1-one), (−)-(1-(2,8-dimethyl-1-thia-3,8-diazaspiro[4.5]dec-3-yl)-3-(1H-indol-3-yl)propan-1-one), dimethyl-1-oxa-3,8-diazaspiro[4.5]dec-3-yl)-3-(1H-indol-3-yl)-propan-1-one, (+)-1-(2,8-dimethyl-1-oxa-3,8-diazaspiro[4.5]dec-3-yl)-3-(1H-indol-3-yl)-propan-1-one, and (−)-1-(2,8-dimethyl-1-oxa-3,8-diazaspiro[4.5]dec-3-yl)-3-(1H-indol-3-yl)-propan-1-one.

There is also provided, in accordance with embodiments of the invention, a pharmaceutical composition comprising a compound as described herein, and a pharmaceutically acceptable carrier, excipient or diluent therefore.

There is also provided, in accordance with embodiments of the invention, a method of treating Alzheimer's Disease, comprising administering to a patient in need of such treatment an effective amount of a compound as described herein.

There is also provided, in accordance with embodiments of the invention, a method of treating insulin resistance syndrome, comprising administering to a patient in need of such treatment an effective amount of a compound as described herein.

There is also provided, in accordance with embodiments of the invention, a method of treating type 2 diabetes, comprising administering to a patient in need of such treatment an effective amount of a compound as described herein.

There is also provided, in accordance with embodiments of the invention, a method of treating a disease or condition which is susceptible to treatment with an M1 muscarinic receptor modulator, comprising administering to a patient in need thereof a therapeutically effective amount of a compound as described herein. In some embodiments, the disease or condition is selected from the group consisting of brain amyloid-mediated disorders; GSK3β-mediated disorders; abnormalities in Wnt-signaling; a tau protein hyperphosphorylation-mediated damage, dysfunction or disease; endogenous growth factor-mediated diseases; a combination of risk factors for AD and/or one of the aforementioned diseases, e.g. head injury, oxidative stress, free radicals, apoptosis, inflammation, exogenous or endogenous toxins, excitotoxins, genetic predisposition, immune or autoimmune dysfunctions or diseases (e.g. lupus, multiple sclerosis, Sjogren's syndrome, chronic fatigue syndrome, fibromyalgia); and diseases states involving disturbances in which a cholinergic dysfunction has been implicated. In some embodiments the disease or condition is selected from the group consisting of AD, Lewy body dementia, cerebral amyloid angiopathy (CAA), cerebral amyloidosis, fronto-temporal dementia, vascular dementia, hyperlipidemia, hypercholesterolemia, fronto-temporal dementia, vascular dementia, multiifract dementia (MID), stroke ischemia, MID combined with stroke/ischemialhead injury, combined MID and AD, mixed AD and PD, human head injury, age-associated memory impairments, mild cognitive impairment (MCI), MCI conducive to AD, bipolar disorder, mania, acute confusion disorder, attention deficit disorder, hallucinatory-paranoid states, emotional and attention disorders, post-operative delirium (anticholinergic syndrome following general anesthesia), antagonism of adverse effects (such as xerostomia, anomia, memory loss and/or confusion, psychosis) of tricyclic antidepressants or of certain drugs (e.g. trihexyphenidyl) used in treating schizophrenia and PD, schizophrenia, bipolar disorder, mania, tardive dyskinesia, congenital ornithine transcarbamylase deficiency, ollivopontocerebral atrophy, alcohol withdrawal symptoms, Huntington's chorea, Pick's disease, Friedrick's ataxia, Gilles de la Tourette disease, and Down's syndrome.

DEFINITIONS

Figure 1A:
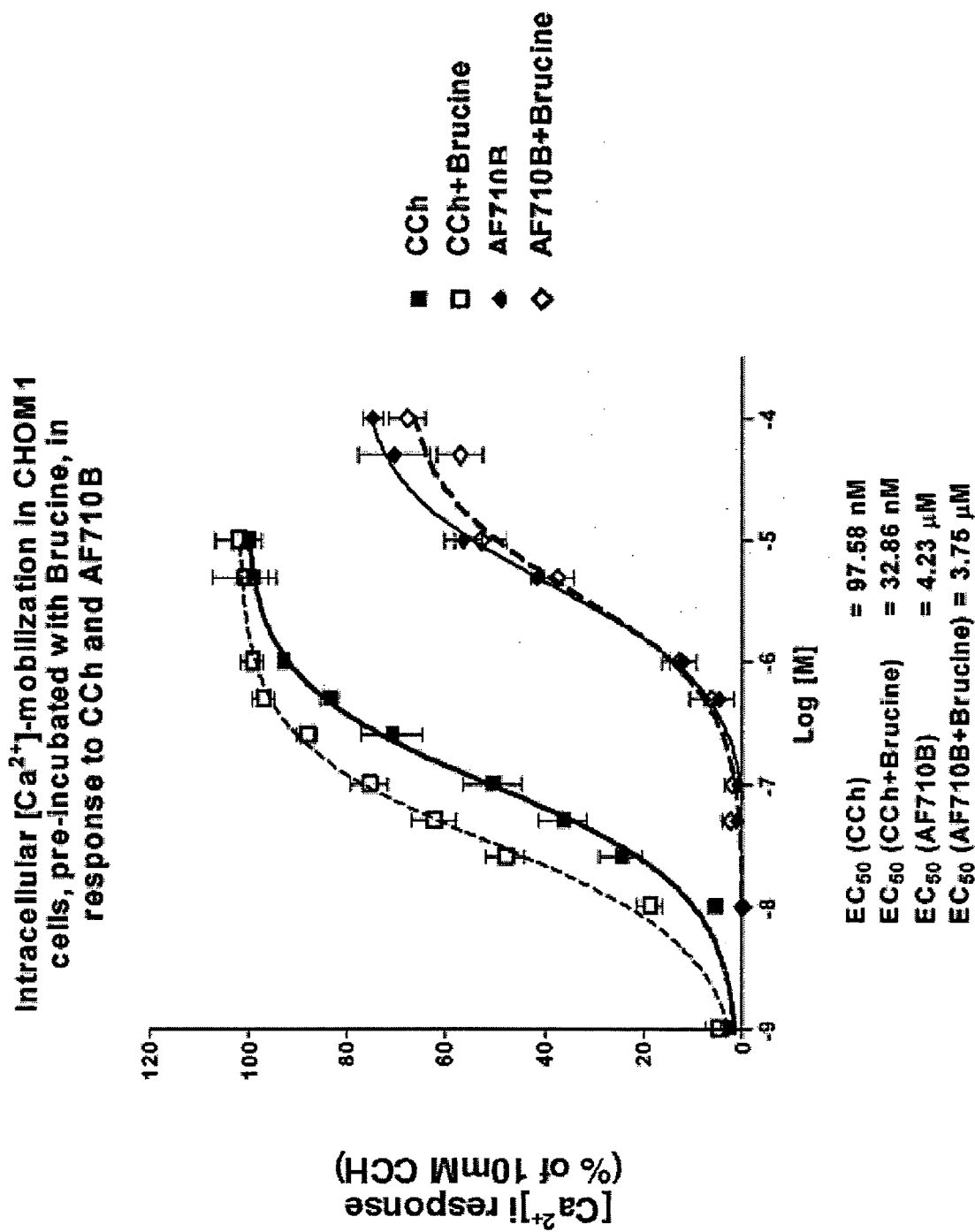
FIGS. 1A and 1B show the results of binding studies using a compound in accordance with embodiments of the invention.

Throughout this specification the terms and substituents retain their definitions.

Alkyl is intended to include linear, branched, or cyclic hydrocarbon structures and combinations thereof. When not otherwise restricted, the term refers to alkyl of 20 or fewer carbons. Lower alkyl refers to alkyl groups of 1, 2, 3, 4, 5 and 6 carbon atoms. Examples of lower alkyl groups include methyl, ethyl, propyl, isopropyl, butyl, s- and t-butyl and the like. Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like.

$C_1$ to $C_{20}$ Hydrocarbon (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) includes alkyl, cycloalkyl, alkenyl, alkynyl, aryl and combinations thereof. Examples include benzyl, phenethyl, cyclohexylmethyl, camphoryl and naphthylethyl. The term "phenylene" refers to ortho, meta or para residues of the formulae:

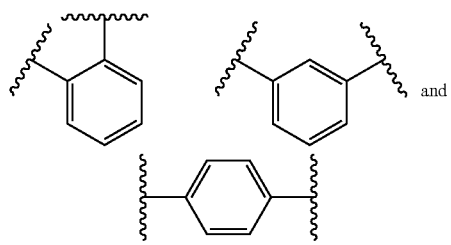

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purposes of the present patent application alkoxy also includes methylenedioxy and ethylenedioxy in which each oxygen atom is bonded to the atom, chain or ring from which the methylenedioxy or ethylenedioxy group is pendant so as to form a ring. Thus, for example, phenyl substituted by alkoxy may be, for example,

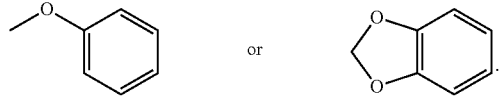

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl.

Acyl refers to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons.

Aryl and heteroaryl refer to aromatic or heteroaromatic rings, respectively, as substituents. Heteroaryl contains one, two or three heteroatoms selected from O, N, or S. Both refer to monocyclic 5- or 6-membered aromatic or heteroaromatic rings, bicyclic 9- or 10-membered aromatic or heteroaromatic rings and tricyclic 13- or 14-membered aromatic or heteroaromatic rings. Aromatic 6, 7, 8, 9, 10, 11, 12, 13 and 14-membered carbocyclic rings include, e.g., benzene, naphthalene, indane, tetralin, and fluorene and the 5, 6, 7, 8, 9 and 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, alkyl, acyl, alkoxyalkyl, hydroxyloweralkyl, phenyl, heteroaryl, benzenesulfonyl, hydroxy, loweralkoxy, haloalkoxy, carboxy, carboalkoxy (also referred to as alkoxycarbonyl), alkoxycarbonylamino, carboxamido (also referred to as alkylaminocarbonyl), cyano, carbonyl, acetoxy, nitro, amino, alkylamino, dialkylamino, mercapto, alkylthio, sulfoxide, sulfone, sulfonylamino, acylamino, amidino, aryl, benzyl, heterocyclyl, phenoxy, benzyloxy, heteroaryloxy, hydroxyimino, alkoxyimino, oxaalkyl, aminosulfonyl, trityl, amidino, guanidino, ureido, and benzyloxy.

The term "halogen" means fluorine, chlorine, bromine or iodine.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

The terms "methods of treating or preventing" mean amelioration, prevention or relief from the symptoms and/or effects associated with the recited disease, state or condition. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

Throughout this application, various publications are referred to. Each of the patents, patent applications, patent publications, and other publications mentioned herein is hereby incorporated by reference in its entirety.

The term "mammal" is used in its dictionary sense. The term "mammal" includes, for example, mice, banisters, rats, cows, sheep, pigs, goats, and horses, monkeys, dogs, cats, rabbits, guinea pigs, and primates, including humans.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques.

As used herein, and as would be understood by the person of skill in the art, the recitation of "a compound" is intended to include salts, solvates and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form. Representative suitable salts include those salts formed with acids such as hydrochloric, sulfuric, phosphoric, acetic, succinic, citric, lactic, maleic, fumaric, tartaric, formic, palmitic, benzoic, glutaric, cholic, pamoic, mucic, D-glutamic, d-camphoric, glycolic, phthalic, lauric, stearic, oleic, salicylic, methanesulfonic, benzenesulfonic, sorbic, picric, cinnamic, and like acids.

The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, for example, the formula W is intended to encompass both of the pure enantiomers of that pair:

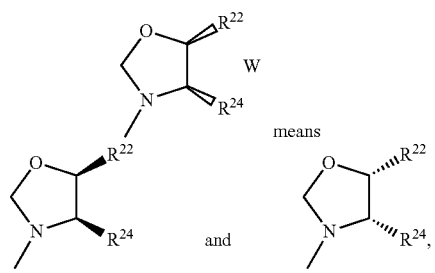

whereas formula X is intended to represent the four diastereomers:

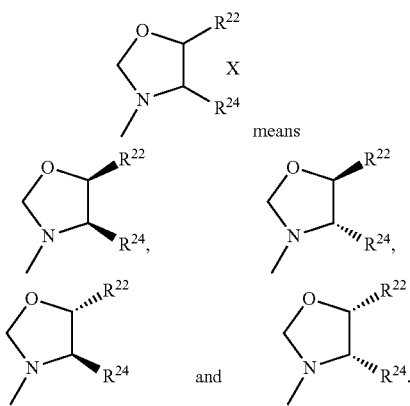

The term "enantiomeric excess" is well known in the art and is defined for a resolution of ab into a+b as $$ee_a = \left( \frac{\text{conc. of } a - \text{conc. of } b}{\text{conc. of } a + \text{conc. of } b} \right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee; in other words, a 90% ee reflects the presence of 95% of one enantiomer and 5% of the other in the material in question.

Unless indicated otherwise, the configuration of any carbon-carbon double bond appearing herein which is not part of a ring is selected for convenience only and is not intended to designate a particular configuration; thus, unless indicated otherwise, a non-ring carbon-carbon double bond depicted arbitrarily herein as E may be Z, E, or a mixture of the two in any proportion. Similarly, all tautomeric forms are intended to be included.

The abbreviations Me, Et, Ph, Tf, Ts and Ms represent methyl, ethyl, phenyl, trifluoromethanesulfonyl, toluenesulfonyl and methanesulfonyl respectively. The following abbreviations and terms have the indicated meanings throughout:
abs=absolute
Ac=acetyl
ACN=acetonitrile
Boc=t-butyloxy carbonyl
Bu=butyl c-=cyclo
CDI=carbodiimide
conc.=concentrated
DCM=dichloromethane=methylene chloride=$CH_2Cl_2$
DCC=dicyclohexylcarbodiimide
DMAP=4-N,N-dimethylaminopyridine
Et=ethyl
FCC=flash column chromatography
GC=gas chromatography
HOBt=hydroxybenzotriazole
HPLC=high performance (or high pressure) liquid chromatograph
i-=iso-
IPA=isopropyl alcohol
Me=methyl
Ph or κ=phenyl
ppt.=precipitate
Pr=propyl
rt=room temperature
sat'd=saturated
s-=secondary
t-=tertiary
TEA=triethylamine
THY=tetrahydrofuran
TLC=thin-layer chromatography
TMS=trimethylsilyl
tosyl=p-toluenesulfonyl A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

Compounds of formula I are M1 mAChR modulators, i.e. they bind to M1 mAChR and act as either agonists or antagonists of this receptor. In some cases the modulation is allosteric, in some cases orthosteric, and in some cases both.

While it may be possible for compounds of formula I to be administered as the raw chemical, it will often be preferable to present them as part of a pharmaceutical composition (also referred to herein as a formulation). In accordance with an embodiment of the present invention there is provided a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

Furthermore, as stated above, the term "compound" includes salts thereof as well, so that independent claims reciting "a compound" will be understood as referring to salts thereof as well. Nevertheless, if in an independent claim reference is made to "a compound or a pharmaceutically acceptable salt thereof", it will be understood that claims which depend from that independent claim which refer to such a compound also include pharmaceutically acceptable salts of the compound, even if explicit reference is not made to the salt in the dependent claim.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques. "Pharmaceutically acceptable carrier" also encompasses controlled release means.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

It should be understood that in addition to the ingredients particularly mentioned above, the formulations of this invention may include other agents conventional in the art having regard to the type of formulation in question, for example those suitable for oral administration may include flavoring agents.

The dose range for adult humans is generally from 0.005 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

For additional information about pharmaceutical compositions and their formulation, see, for example, Remington: The Science and Practice of Pharmacy, 20$^{th}$ Edition, 2000.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered locally. The agents can be coated on a stent. The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form of a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasaly using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants which include but are not limited to bile salts and those described in U.S. Pat. No. 6,524,557 and references therein. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation. Also suitable in the invention are dry powder formulations comprising a therapeutically effective amount of active compound blended with an appropriate carrier and adapted for use in connection with a dry-Powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. No. 5,230,884, U.S. Pat. No. 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. No. 5,348,730, U.S. Pat. No. 6,436,367, WO 91/04011, and U.S. Pat. No. 6,294,153 and U.S. Pat. No. 6,290,987 describes a liposomal based formulation that can be administered via aerosol or other means. Powder formulations for inhalation are described in U.S. 20030053960 and WO 01/60341. The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowis' American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowis and Remington.

It will also be appreciated that in accordance with some embodiments of the present invention, compounds of formula I may be used in combination with other active agents. Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

Table 1 lists compounds representative of embodiments of the invention.

It will be appreciated that as M1 muscarinic receptor modulators, compounds in accordance with embodiments of the invention may be used to treat in a mammal diseases associated with impaired cholinergic function or diseases where there is an imbalance in cholinergic function, or diseases with impared activity of acetylcholine receptors from the group consisting of senile dementia of Alzheimer's type; Alzheimer's disease (AD); Lewy body dementia; mixed Alzheimer's and Parkinson's disease; multiifract dementia (MID); fronto-temporal dementia; vascular dementia; stroke/ischemia, MID combined with stroke/ischemia/head injury; combined MID and AD; human head injury; age-associated memory impairments; mild cognitive impairment (MCI); MCI conducive to AD; cognitive dysfunction (including forgetfulness, acute confusion disorders, attention-deficit disorders, focus and concentration disorders); hallucinatory-paranoid states; emotional and attention disorders; sleep disorders; post-operative delirium; adverse effects of tricyclic antidepressants; adverse effects of certain drugs used in the treatment of schizophrenia and Parkinson's disease; xerostomia, anomia, memory loss and/or confusion; psychosis; schizophrenia, schizophrenia comorbit with AD, late onset schizophrenia, paraphrenia, schizophreniform disorders; anxiety; bipolar disorders; mania; mood stabilization; cognitive impairments after removal of certain gliomas; tardive dyskinesia; oxidative stress during oxygen therapy; aphasia; postencephalitic amnesic syndrome; AIDS dementia; memory impairments in autoimmune diseases including lupus, multiple sclerosis, Sjogren's syndrome, chronic fatigue syndrome, and fibromyalgia; memory impairments in atypical depression or schizophrenia; pain, rheumatism, arthritis and terminal illness; xerophtalmia, vaginal dryness, skin dryness; immune dysfunctions; neurocrine disorders and dysregulation of food intake, including bulimia and anorexia; obesity; congenital ornithine transcarbamylase deficiency; ollivopontocerebral atrophy; alcohol withdrawal symptoms; substance abuse including withdrawal symptoms and substitution therapy; Huntington's chorea; progressive supranuclear palsy; Pick's disease; Friedrick's ataxia; Gilles de la Tourette disease; Down's syndrome; glaucoma; presbyopia; autonomic disorders including dysfunction of gastrointestinal motility and function such as inflammatory bowel disease, irritable bowel syndrome, diarrhea, constipation, gastric acid secretion and ulcers; urinary urge incontinence, asthma, COPD. Compounds in accordance with embodiments of the invention may also be used in the preparation of medicaments for such treatment.

Similarly, it will be appreciated that as M1 muscarinic receptor modulators, compounds in accordance with embodiments of the invention may be used for preventing or treating central or peripheral nervous system disease states due to dysfunction in one or more of the following: brain, nervous system, cardiovascular system, immune system, neurocrine system, gastrointestinal system, or endocrine and exocrine glands, eye, cornea, lungs, prostate, or other organs where the cholinergic function is mediated by muscarinic receptor subtypes, wherein said dysfunction involves: brain amyloid-mediated disorders; glycogen synthase kinase (GSK3p)-mediated disorders; tau protein hyperphosphorylation-mediated damages, dysfunctions or diseases; CNS and PNS hypercholesterolemia- and/or hyperlipidemia-mediated damages, dysfunctions or diseases; Wnt-mediated signaling abnormalities; impairment of neuroplasticity; hyperglycemia; diabetes; endogenous growth factors-mediated diseases, or combination of additional risk factors; or disease states that involve apolipoprotein E; or disturbances in which a cholinergic dysfunction has been implicated, including: senile dementia of Alzheimer's type, Alzheimer's disease (AD), delay of onset of AD symptoms in a patient at risk for developing AD, Lewy body dementia, cerebral amyloid angiopathy (CAA), cerebral amyloidosis, fronto-temporal dementia, vascular dementia, hyperlipidemia, hypercholesterolemia, multiifract dementia (MID), stroke ischemia, MID combined with stroke/ischemia/head injury, combined MID and Alzheimer's disease, human head injury, age-associated memory impairments, mild cognitive impairment (MCI), MCI conducive to AD, bipolar disorder, mania, schizophrenia, nonaffective sychozophrenia, paraphrenia, immune dysfunctions, neurocrine disorders and dysregulation of food intake, including bulimia and anorexia, weight control, obesity, inflammation. Compounds in accordance with embodiments of the invention may also be used in the preparation of medicaments for such treatment.

Synthetic Methods

In general, compounds of formula I may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Processes for obtaining compounds of formula I are presented below. Other compounds of formula I may be prepared in analogous fashion to those whose synthesis is exemplified herein. The procedures below illustrate such methods. Furthermore, although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Compounds of formula I may be synthesized from the corresponding spiro compounds in which H is present instead of $R^5$, as illustrated in Scheme 1 below:

Scheme 1

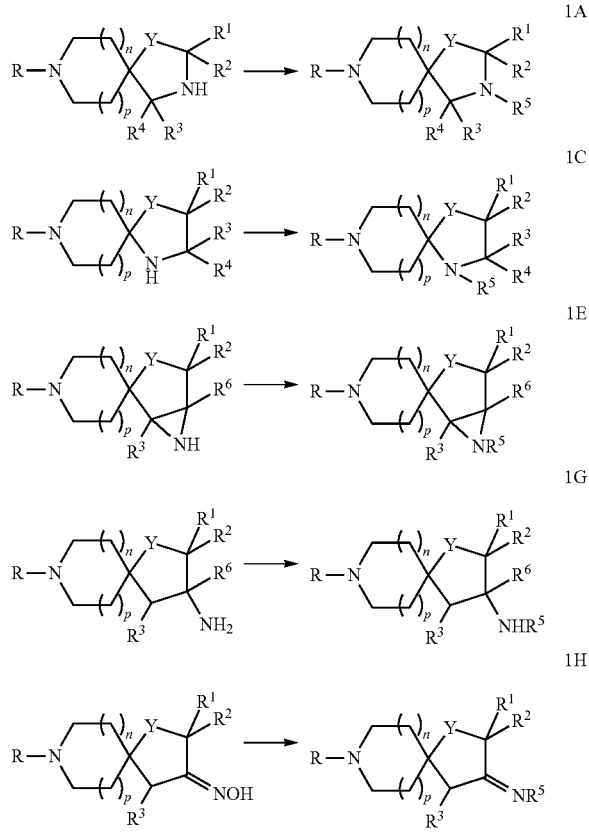

Coupling of amines and 3-indolecarboxylic acid may proceed via activation of the acid moiety by either dicyclohexylcarbodiimide (DCC) or a combination of DCC and 1-hydroxybenzotriazole (HOBT). The coupling of amines and 3,5-di-tert-butyl-4-hydroxybenzoic acid may proceed via activation of the acid moiety by combination of DCC and 1-hydroxybenzotriazole (HOBT). Coupling of amines and valproyl chloride or p-fluorobenzenesulfonyl chloride to yield the corresponding substituted amine may be effected in the presence of base (triethylamine or sodium hydride).

The precursor amine compounds may in turn be prepared as described in greater detail below. Thus, for example, 2,8-Dimethyl-1-oxa-3,8-diaza-spiro[4.5]decane may be obtained by reaction of 4-aminomethyl-1-methyl-piperidin-4-ol with acetaldehyde in dry dichloromethane. 2,8-Dimethyl-1-oxa-4,8-diazaspiro[4.5]decane may be obtained by reaction of 1-amino-2-propanol with 1-methyl-4-piperidone under reflux. 1',4-Dimethylspiro[3-oxa-6-azabicyclo[3.1.0]hexane-2,4'-piperidine] may be obtained by first preparing 2,8-dimethyl-1-oxa-8-azaspiro[4.5]decan-3-one oxime from 1-methyl-4-piperidone via 2,8-dimethyl-1-oxa-8-azaspiro[4.5]decan-3-one per the procedure of Tsukamoto et. al., Chem. Pharm. Bull. 1995, 43, 842-852, followed by reduction of the oxime with Red-Al (sodium bis(2-methoxyethoxy)aluminumhydride) and then basic workup to yield 1',4-Dimethylspiro[3-oxa-6-azabicyclo[3.1.0]hexane-2,4'-piperidine]. 2,8-Dimethyl-1-oxa-8-aza-spiro[4.5]dec-3-ylamine may be obtained by first preparing 2,8-dimethyl-1-oxa-8-azaspiro[4.5]decan-3-one oxime from 1-methyl-4-piperidone via 2,8-dimethyl-1-oxa-8-azaspiro[4.5]decan-3-one per the procedure of Tsukamoto et. al., Chem. Pharm. Bull. 1995, 43, 842-852, followed by reduction of the oxime with lithium aluminum hydride/aluminum chloride. Compounds of formula I may then be prepared from these amines by an appropriate coupling reaction.

In preparing compounds of formula I, methods known to organic chemists may be employed, such as methods for the formation of the five-membered rings, ring-substitution, changing the degree of ring saturation/unsaturation, interconvertion of salts and bases, and so forth. In these synthetic methods, the starting materials can contain a chiral center and, when a racemic starting material is employed, the resulting product is generally a mixture of R and S enantiomers. Alternatively, a chiral isomer of the starting material can be employed and, if the reaction protocol employed does not racemize this starting material, a chiral product is obtained. Such reaction protocols can involve inversion of the chiral center during synthesis. In cases where racemates or diastereomeric mixtures are obtained, the different stereoisomeric forms may be separated from each other by methods known in the art. Alternatively a given isomer may be obtained by stereospecific or asymmetric synthesis. It will be appreciated, therefore, that while exemplary methods of preparing certain compounds of the invention will be described, other methods can also be applied to preparation of the present compounds, as will be known by skilled person.

EXAMPLES

In order to facilitate preparation of new compounds in accordance with embodiments of the invention, several rigid bicyclic spiro-structures were synthesized:

2,8-Dimethyl-1-thia-3,8-diaza-spiro[4.5]decane was obtained from reduction of 2,8-dimethyl-1-thia-3,8-diaza-spiro[4.5]dec-2-ene with sodium cyanoborohydride in methanol.

2,8-Dimethyl-1-oxa-3,8-diaza-spiro[4.5]decane was obtained by the reaction of 4-aminomethyl-1-methyl-piperidin-4-ol with acetaldehyde in dry dichloromethane.

2,8-Dimethyl-1-oxa-4,8-diazaspiro[4.5]decane was obtained by the reaction of 1-amino-2-propanol with 1-methyl-4-piperidone under reflux.

1',4-Dimethylspiro[3-oxa-6-azabicyclo[3.1.0]hexane-2, 4'-piperidine] was obtained in several steps. First, 2,8-dimethyl-1-oxa-8-azaspiro[4.5]decan-3-one oxime was prepared from 1-methyl-4-piperidone via 2,8-dimethyl-1-oxa-8-azaspiro[4.5]decan-3-one according to the procedure of Tsukamoto et. al., Chem. Pharm. Bull. 1995, 43, 842-852. Reduction of the oxime with Red-Al followed by basic workup yielded the title compound.

2,8-Dimethyl-1-oxa-8-aza-spiro[4.5]dec-3-ylamine was obtained in several steps. First, 2,8-dimethyl-1-oxa-8-azaspiro[4.5]decan-3-one oxime was prepared from 1-methyl-4-piperidone via 2,8-dimethyl-1-oxa-8-azaspiro[4.5]decan-3-one according to the procedure of Tsukamoto et. al., Chem. Pharm. Bull. 1995, 43, 842-852. Reduction of the oxime with LiAlH$_4$/AlCl$_3$ yielded the title compound.

2,8-dimethyl-1-thia-8-aza-spiro[4.5]dec-3-ylamine was obtained in several steps. First, 2,8-dimethyl-1-thia-8-azaspiro[4,5]dec-3-one oxime was prepared from 1-methyl-4-piperidone via 2,8-dimethyl-1-thia-8-azaspiro[4.5]decan-3-one. Reduction of the oxime with Red-Al followed by basic workup yielded the title compound.

Unless otherwise noted, reagents and solvents were used as received from commercial suppliers. Proton nuclear magnetic resonance (NMR) spectra were obtained on Bruker Avance-300 and Bruker-500 spectrometers at 300 or 500 MHz, respectively. Spectra are reported in ppm (δ) and coupling constants, J, are reported in Hertz. Tetramethylsilane (TMS) was used as an internal standard. The following abbreviations are used in reporting the NMR data: s=singlet, d=doublet, t=triplet, q=quartet, m=multiplet, br=broad. $^{13}$C-NMR spectra were recorded with Bruker Avance-300 and Bruker-500 spectrometers. Mass spectra were collected using a UG 70 USEQ mass spectrometer. GC-MS spectra were recorded with Varian Saturan 2000 GC-MS/MS spectrometer. Infrared (IR) spectra were recorded on a Nicolet 380 FT-IR spectrophotometer with Smart Multi-Bounce ZnSe HATR. All solvents and reagents were analytical grade. Analysis of chemical purity of our NCE was recorded with HPLC FINNIGAN Surveyor.

Example 1

Synthesis of
2,8-dimethyl-1-thia-3,8-diazaspiro[4.5]decane

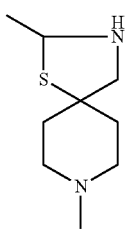

To a stirred solution of 2,8-dimethyl-1-thia-3,8-diaza-spiro [4.5]dec-2-ene (10.4 ml, 60 mmol) in methanol (150 ml) at room temperature, bromocresol green (5 mg) was added and the solution became blue. 4N HCl/MeOH was added to the stirred solution until the color changed to yellow. Sodium cyanoborohydride (3.9 gr, 62 mmol) was then added in one portion and the resulting mixture was stirred at room temperature for 2 h. During this period, each time that the reaction color changed to green, more 4N HCl/MeOH was added to keep the solution color yellow. At the end of this time, the solvent was evaporated under reduced pressure to give blue-green oil. Dichloromethane (100 ml) was added to the residue and the mixture was washed with 2N NaOH (50 ml). The two phases were separated and the aqueous phase was extracted with dichloromethane (100 ml). The organic phases were combined, dried with anhydrous magnesium sulfate, filtered and the solvent was evaporated under reduced pressure. The residue was purified by flash chromatography (silica, CH$_2$Cl$_2$/MeOH/NH$_4$OH 90/10/1) to give the title compound (2.18 g) as an almost colorless oil. $^1$H NMR (CDCl$_3$, 500 MHz) δ 4.61 (q, J=6.18 Hz, 1H, CHCH$_3$), 3.10 (d, J=12.6 Hz, 1H, CHHNH), 2.74 (d, J=12.6 Hz, 1H, CHHNH), 2.27-2.19 (m, 1H), 2.23 (s, 3H, NCH$_3$), 2.10 (m, 2H), 1.85-1.70 (m, 5H), 1.46 (d, J=6.18 Hz, 3H, CH$_3$CH) ppm.

Example 2

Synthesis of
2,8-dimethyl-1-oxa-3,8-diaza-spiro[4.5]decane

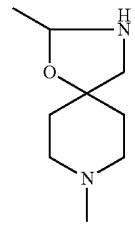

To a solution of 4-aminomethyl-1-methyl-piperidin-4-ol (2.127 g, 14.77 mmol) in dichloromethane (15 ml) was added anhydrous magnesium sulfate (2.9 g). The resulting mixture was cooled to 0° C. and freshly distilled acetaldehyde (835 µl, 14.78 mmol) was added. After 6 h of stirring at room temperature, the mixture was filtered and the solvent was evaporated under reduced pressure to give the title compound (2.16 g) as an almost colorless liquid. $^1$H NMR (CDCl$_3$, 500 MHz) δ 4.60 (q, J=5.40 Hz, 1H, CHCH$_3$), 3.01 (d, J=12 Hz, 1H, CHHNH), 2.76 (d, J=12 Hz, 11-1, CHHNH), 2.55-2.31 (m, 4H, CH$_2$N), 2.28 (s, 3H, NCH$_3$), 1.77-1.58 (m, 4H, CH$_2$CO), 1.36 (d, J=5.40 Hz, 3H, CH$_3$CH) ppm; $^{13}$C NMR (CDCl$_3$, 300 MHz) δ 87.57 (CH), 57.19 (CH$_2$), 53.14 (C), 52.96 (CH$_2$), 46.15 (CH$_3$), 37.28 (CH$_2$), 35.73 (CH$_2$), 20.32 (CH$_3$) ppm.

Example 3

Synthesis of 2,8-dimethyl-1-oxa-4,8-diazaspiro[4.5]decane

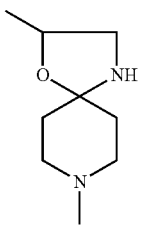

A mixture of 1-amino-2-propanol (9.2 ml, 1.2 mmol) and 1-methyl-4-piperidone (11.5 ml, 1.0 mmol) was heated under reflux for 2 h and left overnight at room temperature. The reaction mixture was distilled under reduced pressure (~15 mm Hg). The title compound was collected at 82-95° C. $^1$H NMR (CDCl$_3$, 300 MHz) δ 4.02 (m, 1H, OCH), 3.25 (dd, J=11.9, 6.3 Hz, 1H, CHH), 2.68 (dd, J=11.9, 6.6 Hz, 1H, CHH), 2.4-2.6 (m, 4H-piperidine), 2.1 (s, 3H, NCH$_3$), 1.65-1.81 (m, 4H-piperidine), 1.21 (d, J=6.1 Hz, 3H, CH$_3$CH) ppm.

Example 4

Synthesis of 1',4-dimethyl-spiro-(3-oxa-6-azabicyclo[3.1.0]hexane-2,4'-piperidine)

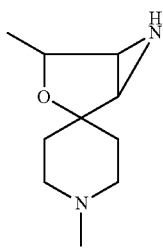

Red-Al (65% solution in toluene, 5.4 ml) was added dropwise to a solution of 2,8-dimethyl-1-oxa-8-aza-spiro[4.5]decan-3-one oxime (1.5 gr, 7.6 mmol) in dry THF (39 ml) and the reaction mixture was stirred overnight at room temperature. The reaction mixture was cooled (ice-water) and decomposed by successive additions of water (1.6 ml), 15% aqueous NaOH (1.6 ml) and water (4.6 ml). Tetrahydrofuran (THF) (40 ml) was added and the solids were filtered off over Celite. The THF filtrate was concentrated under reduced pressure. The residual oil was dissolved in dichloromethane, dried and evaporated. Flash chromatography (silica, CHCl$_3$/MeOH/NH$_4$OH 60/40/1) of the residue gave the title amine (apparently as two isomers). $^1$H-NMR (D$_2$O/CDCl$_3$, 300 MHz) δ 4.13 and 4.06 (two q, J=6.7 and J=6.2 Hz, 1H, two OCH), 2.54-2.33 (m, 6H), 2.27 (s, 3H, NCH$_3$), 1.77-1.65 (m, 4H), 1.24 and 1.20 (two d, J=6.7 and J=6.2 Hz, 3H, CH$_3$) ppm; GC-MS (CI) 6.95 min −183(M+1) and 6.64 min −183(M+1) for C$_{10}$H$_{18}$N$_2$O.

Example 5

Synthesis of 1-(2,8-dimethyl-1-thia-3,8-diazaspiro[4.5]dec-3-yl)-3-(1H-indol-3-yl) propan-1-one (AF710)

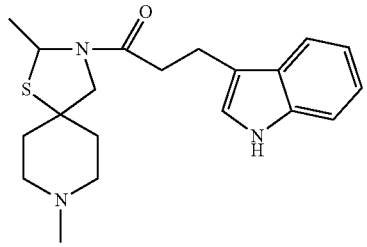 [SMILES: CC1SC2(CCN(C)CC2)CN1C(=O)CCc1c[nH]c2ccccc12]

To a stirred solution of 2,8-dimethyl-1-thia-3,8-diaza-spiro[4.5]decane (2.18 g, 11.7 mmol) in dichloromethane (230 ml) at room temperature was added dicyclohexylcarbodiimide (DCC) (3.24 g, 15.7 mmol) followed by addition of 3-indolepropionic acid (2.87 g, 15.2 mmol). The resulting solution was stirred at room temperature overnight. During the reaction a white solid precipitated. After filtration the solvent was evaporated and the crude product was purified by flash chromatography (silica, CH$_2$Cl$_2$/EtOH/NH$_4$OH 90/10/1) to give AF710 (2.5 g, 100% chemical purity) as a white solid. $^1$H NMR (CDCl$_3$, 300 MHz) δ 8.17 (br s, 1H, NH-indole), 7.60 (d, J=7.81 Hz, 1H, CHC arom), 7.35 (d, J=8.08 Hz, 1H, CHC arom), 7.19 (app t, J=7.53 Hz, 1H, CHCH arom), 7.12 (app t, J=7.45 Hz, 1H, CHCH arom), 7.02 (d, J=1.86 Hz, 1H, CHNH arom), 5.52, 5.09 (2q, J=6.15 and J=6.22 Hz, 1H, CHCH$_3$), 4.62, 3.66 (2d, J=11.76 and J=11.5 Hz, 1H, CHHNCO), 3.29, 3.08 (2d, J=11.48 and J=12.0 Hz, 1H, CHHNCO), 3.18-3.11 (m, 2H), 2.72-2.66 (m, 2H), 2.64-2.46 (m, 2H), 2.26, 2.25 (2s, 3H, NCH$_3$), 2.32-2.19, 2.12-2.02 (2m, 2H), 1.87-1.80, 1.68-1.51 (2m, 4H), 1.48, 1.43 (2d, J=6.21 and J=6.19 Hz, 3H, CH$_3$—CH) ppm; $^{13}$C NMR (CDCl$_3$, 500 MHz) δ 170.58 (C), 136.39 (C), 127.25 (C), 122.19 (CH), 121.80 (CH), 119.52 (CH), 118.73 (CH), 115.17 (C), 111.31 (CH), 57.48, 57.19 (CH), 55.46 (C), 54.55, 54.12 (CH$_2$), 53.11, 52.86 (CH$_2$), 46.21, 46.15 (CH$_3$), 38.05, 37.32 (CH$_2$), 36.82, 36.31 (CH$_2$), 34.41 (CH$_2$), 25.44, 23.47 (CH$_3$), 21.04, 20.96 (CH$_2$) ppm.

Example 6

Chiral Separation of AF710A and AF710B

The separation of AF710 to its enantiomers was done by HPLC on a semipreparative column. 200 μl of a solution of AF710 in methanol (50 mg/ml) was injected into the column and eluted therethrough. Following elution, the eluent was evaporated to dryness.
HPLC: Merck-Hitachi model L-62000A
Detector: Merck-Hitachi model L-4250
Column: Chiralcel OJ-H, 250×10 mm
Flow rate: 4 ml/min
Column Temp: room temperature
Mobile phase: Hexane/Ethanol 85:15
Concentration: 50 mg/ml
UV Detection: 255 nm
First eluting enantiomer (AF710A): 99% ee; specific rotation [α]=+60° (C=0.415, Methanol)
Second eluting enantiomer (AF710B): 99% ee; specific rotation [α]=−56° (C=0.303, Methanol)

Example 7

Synthesis of 3-(4-fluorobenzenesulfonyl)-2,8-dimethyl-1-thia-3,8-diazaspiro[4.5]-decane (AF716)

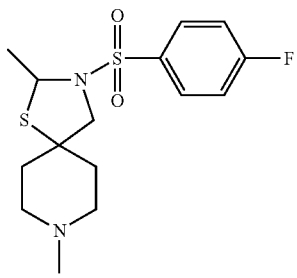 [SMILES: CC1SC2(CCN(C)CC2)CN1S(=O)(=O)c1ccc(F)cc1]

2,8-dimethyl-1-thia-3,8-diaza-spiro[4.5]decane (573 mg, 3.08 mmol) was dissolved in dry dichloromethane (2 ml) under an argon atmosphere. Distilled triethylamine (644 µl, 4.62 mmol) was added and the resulting solution was cooled to 0° C. A solution of p-fluorobenzenesulfonyl chloride (600 mg, 3.08 mmol) in dry dichloromethane (2 ml) was added dropwise with a syringe. The reaction flask was allowed to warm to room temperature with stirring, and a white solid started to precipitate. After 1 h of stirring, dichloromethane (50 ml) was added and the resulted solution was washed with water (2×10 ml). The organic phase was dried with anhydrous magnesium sulfate, filtered and evaporated to give the crude mixture as an oil. The crude product was purified by flash chromatography (silica, $CH_2Cl_2$/MeOH/$NH_4OH$ 93/7/1) to provide AF716 (496 mg, 98.8% chemical purity) as an off-white powder. $^1$H NMR ($CDCl_3$, 300 MHz) δ 7.89-7.85 (m, 2H, two $CHCSO_2$), 7.27-7.19 (m, 2H, CHCF), 5.02 (q, J=6.12 Hz, 1H, CH—$CH_3$), 3.66 (d, J=11.37 Hz, 1H, CHHNS), 3.48 (d, J=11.37 Hz, 1H, CHHNS), 2.72-2.50 (m, 2H, $CH_2NCH_3$), 2.25 (s, 3H, $NCH_3$), 2.16-2.07 (m, 2H, $CH_2NCH_3$), 1.95-1.88 (m, 2H, $CH_2CS$), 1.55 (d, J=6.12 Hz, 3H, $CH_3CH$), 1.48 (m, 2H, $CH_2CS$) ppm; $^{13}$C NMR ($CDCl_3$, 300 MHz) δ 166.92 and 163.54 (C), 130.05 (CH), 129.93 (CH), 129.58 (C), 116.60 (CH), 116.30 (CH), 60.76 (C), 60.24 (CH), 54.05 ($CH_2$), 53.22 ($CH_2$), 46.03 ($CH_3$), 37.16 ($CH_2$), 37.05 ($CH_2$), 25.56 ($CH_3$) ppm.

Example 8

Synthesis of 1-(2,8-dimethyl-1-thia-3,8-diazaspiro[4.5]dec-3-yl)-2-propylpentan-1-one (AF717)

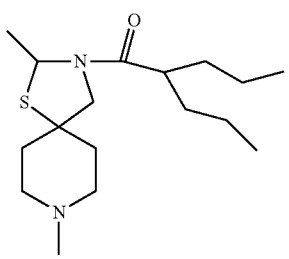 [SMILES: CCCC(CCC)C(=O)N1CC2(CCN(C)CC2)SC1C]

2,8-dimethyl-1-thia-3,8-diaza-spiro[4.5]decane (982 mg, 5.28 mmol) was dissolved in dry dichloromethane (5 ml) under argon atmosphere. Distilled triethylamine (1.10 ml, 7.92 mmol) was added and the resulting solution was cooled to 0° C. Valproyl chloride (910 mg, 5.60 mmol) was added dropwise with a syringe. The reaction flask was allowed to warm to room temperature with stirring, and white solid started to precipitate. After 4 h of stirring, dichloromethane (100 ml) was added and the resulting solution was washed with water (10 ml). The two phases were separated and the aqueous phase was extracted with dichloromethane (2×50 ml). The combined organic phase was dried with sodium sulfate, filtered and evaporated under reduced pressure. The residue was purified by flash chromatography (silica, $CH_2Cl_2$/EtOH/$NH_4OH$ 150/10/1) to give AF717 (521 mg, 99.2% chemical purity) as an off-white powder. $^1$H NMR ($CDCl_3$, 300 MHz) δ 5.53, 5.26 (2q, J=6.12 and J=6.3 Hz, 1H, $CHCH_3$), 4.67, 3.90 (2d, J=12.0 and J=11.35 Hz, 1H, CHHNCO), 3.48, 3.09 (2d, J=11.35 and J=12.0 Hz, 1H, CHHNCO), 2.78-2.59 (m, 2H, $CH_2N$), 2.53-2.47 (m, 1H, CHCO), 2.30, 2.19 (2s, 3H, $NCH_3$), 2.15-2.05 (m, 2H, $CH_2N$), 2.02-1.84 (m, 2H, $CH_2CS$), 1.74-1.61 (m, 4H, $CH_2CHCO$), 1.55, 1.50 (2d, J=6.3 and J=6.12 Hz, 3H, $CH_3CH$), 1.44-1.36 (m, 2H, $CH_2CS$), 1.34-1.21 (m, 4H, $CH_2CH_3$), 0.93-0.87 (m, 6 h, $CH_3CH_2$) ppm; $^{13}$C NMR ($CDCl_3$, 300 MHz) δ 174.35, 174.04 (C), 59.13 (C), 57.35, 57.19 (CH), 54.52, 54.06 ($CH_2$), 53.13, 52.77 ($CH_2$), 46.09 ($CH_3$), 43.77, 42.55 (CH), 38.37, 37.58 ($CH_2$), 37.04, 36.20 ($CH_2$), 35.76, 35.35 ($CH_2$), 35.08, 34.77 ($CH_2$), 26.01, 23.01 ($CH_3$), 21.08, 20.98 ($CH_2$), 20.73, 20.56 ($CH_2$), 14.27, 14.22 ($CH_3$) ppm.

Example 9

Synthesis of (3,5-di-tert-butyl-4-hydroxy-phenyl)-(2,8-dimethyl-1-thia-3,8-diaza-spiro[4.5]dec-3-yl)-methanone (AF723)

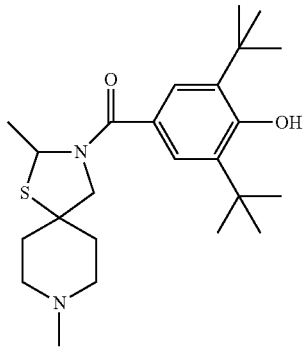 [SMILES: CC1SC2(CCN(C)CC2)CN1C(=O)c1cc(C(C)(C)C)c(O)c(C(C)(C)C)c1]

A solution of dicyclohexylcarbodiimide (985 mg, 4.77 mmol) in dry and distilled dichloromethane (10 ml) was added to a stirred solution of 3,5-di-tert-butyl-4-hydroxybenzoic acid (1.14 g, 4.55 mmol) in dichloromethane (15 ml) at room temperature under an argon atmosphere. Dicyclohexylurea began to precipitate as a white solid. 1-Hydroxybenzotriazole (645 mg, 4.77 mmol) was added and the resulting solution was stirred at room temperature for 5 min. 2,8-dimethyl-1-thia-3,8-diaza-spiro[4.5]decane (846 mg, 4.55 mmol) in dichloromethane (5 ml) was then added and the resulting mixture was kept at room temperature overnight. The next day mixture was heated at 30° C. (temperature of water bath) for 5 hrs and then kept at room temperature for another 4 days. The resulting suspension was filtered and the solvent evaporated under reduced pressure. The residue was purified by flash chromatography (silica, CH$_2$Cl$_2$/EtOH/NH$_4$OH 140/10/1) to give two fractions: AF723 (224 mg, 99.16% chemical purity) and a mixture of AF723 with a by-product (943 mg). The mixture of AF723 with by-product was purified by flash chromatography in a COMBI-flash system using linear gradient (silica, CH$_2$Cl$_2$/EtOH/NH$_4$OH 220/10/1 to 140/10/1). After evaporation and drying under vacuum, AF723 (516 mg, 100% chemical purity) was obtained as a white solid. $^1$H NMR. (CDCl$_3$, 500 MHz) δ 7.27 (s, 2H, arom CH), 5.55 (m, 1H, CH—S), 5.44 (s, 1H, OH), 4.10 (m, 1H, CHH—N—CO), 3.40 (m, 1H, CHH—N—CO), 2.60 (m, 2H, CH$_2$—NCH$_3$), 2.28 (m, 1H, CHH—NCH$_3$), 2.25 (s, 3H, NCH$_3$), 2.11 (m, 1H, CHH—NCH$_3$), 1.95-1.66 (m, 4H, two CH$_2$—CS), 1.60 (d, J=6.15 Hz, 3H, CH$_3$—CH), 1.44 (s, 18H, t-butyl) ppm; $^{13}$C NMR (CDCl$_3$, 500 MHz) δ 170.78 (C=O), 155.52 (C), 135.93 (two C), 127.39 (C), 124.30 (two CH), 59.56 (C), 58.00 (CH), 56.40 (CH$_2$), 54.23 (CH$_2$), 52.82 (CH$_2$), 45.88 (CH$_3$), 37.68 (CH$_2$), 36.50 (CH$_2$), 34.28 (C), 30.21 (CH$_3$), 23.99 (CH$_3$) ppm; FUR(HATR) 2943.89, 1619.92, 1388.67 cm$^{-1}$; GC-MS (EI) 7.31 min m/z: 419 (M+1).

Example 10

Synthesis of 1-(2,8-dimethyl-1-thia-3,8-diaza-spiro [4.5]dec-3-yl)-propan-1-one (AF724)

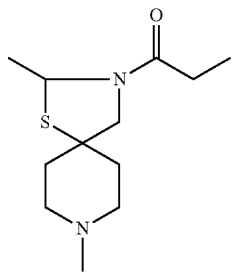 [SMILES: CCC(=O)N1CC2(CCN(C)CC2)SC1C]

To a stirred solution of 2,8-dimethyl-1-thia-3,8-diaza-spiro [4.5]decane (Example 1) (0.86 g, 4.62 mmol) in dichloromethane (90 ml) at room temperature was added dicyclohexylcarbodiimide (DCC) (1.28 g, 6.2 mmol) followed by addition of propionic acid (0.41 ml, 5.5 mmol). The resulting solution was stirred at room temperature overnight. During the reaction a white solid precipitated. After filtration the solvent was evaporated and the crude product was purified by flash chromatography (silica, CH$_2$Cl$_2$/MeOH/NH$_4$OH 90/10/1) to give the title compound (0.5 g) as a colorless oil. $^1$H NMR (CDCl$_3$, 300 MHz) δ 5.51, 5.19 (2q, J=6.15 and J=6.22 Hz, 1H, CHCH$_3$), 4.63, 3.74 (2d, J=11.88 and J=11.57 Hz, 1H, CHHNCO), 3.44, 3.08 (2d, J=11.55 and J=12.09 Hz, 1H, CHHNCO), 2.8-2.6 (m, 2H), 2.5-2.2 (m, 7H, CH$_2$, CH$_2$CH$_3$, NCH$_3$), 2.2-2.0 (m, 1H), 2.0-1.8 (m, 3H) 1.52, 1.48 (2d, J=630 and J=6.18 Hz, 3H, CH$_3$—CH), 1.19-1.12 (m, 3H, CH$_3$) ppm; $^{13}$C NMR (CDCl$_3$, 300 MHz) δ 171.6 (C), 57.5, 57.2 (CH), 55.5 (C), 54.7, 54.3 (CH$_2$), 53.2, 53.0 (CH$_2$), 46.3 (CH$_3$), 38.4, 37.7 (CH$_2$), 37.0, 36.4 (CH$_2$), 28.8, 26.8 (CH$_2$), 25.6, 23.6 (CH$_3$), 9.6, 9.4 (CH$_3$) ppm.

Example 11

Synthesis of 1-(2,8)-dimethyl-1-thia-3,8-diaza-spiro [4.5]dec-3-yl)-4-(1H-indol-3-yl)-butan-1-one (AF725)

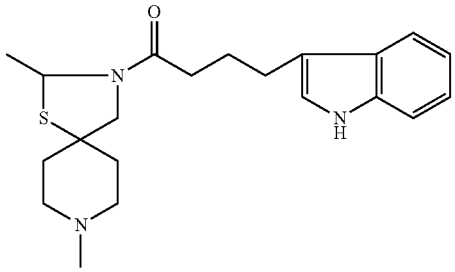 [SMILES: CC1SC2(CCN(C)CC2)CN1C(=O)CCCc1c[nH]c2ccccc12]

To a stirred solution of 2,8-dimethyl-1-thia-3,8-diaza-spiro [4.5]decane (Example 1) (0.97 g, 52 mmol) in dichloromethane (100 ml) at room temperature was added dicyclohexylcarbodiimide (DCC) (1.44 g, 6.98 mmol) followed by addition of 3-indolebutyric acid (1.26 g, 6.22 mmol). The resulting solution was stirred at room temperature overnight. During the reaction a white solid precipitated. After filtration the solvent was evaporated and the crude product was purified by flash chromatography (silica, CH$_2$Cl$_2$/MeOH/NH$_4$OH 90/10/1) to give the title compound (400 mg) as a solid. $^1$H NMR (CDCl$_3$, 300 MHz) δ 8.21 (br s, 1H, NH-indole), 7.60 (d, J=7.75 Hz, 1H, CHC arom), 7.35 (d, J=8.09 Hz, 1H, CHC arom), 7.19 (app t, J=7.45 Hz, 1H, CHCH arom), 7.10 (app t, J=7.43 Hz, 1H, CHCH arom), 6.99 (br s, 1H, CHNH arom), 5.53, 5.08 (2q, J=6.15 and J=6.17 Hz, 1H, CHCH$_3$), 4.65, 3.58 (2d, 0.1=11.96 and J=11.55 Hz, 1H, CHHNCO), 3.32, 3.08 (2d, J=11.59 and J=12.09 Hz, 1H, CHHNCO), 2.87-2.80 (m, 2H), 2.8-2.5 (m, 2H), 2.5-2.18 (m, 3H), 2.27 (s, 3H, NCH$_3$), 2.18-2.0 (m, 3H), 2.0-1.58 (m, 4H), 1.48, 1.43 (2d, J=6.17 and J=6.24 Hz, 3H, CH$_3$—CH) ppm; $^{13}$C NMR (CDCl$_3$, 300 MHz) δ 170.99 (C), 136.54 (C), 127.65 (C), 122.13 (CH), 121.69 (CH), 119.38 (CH), 119.09 (CH), 115.77 (C), 111.33 (CH), 57.57, 57.17 (CH), 55.30 (C), 54.67, 54.23 (CH$_2$), 53.21, 52.92 (CH$_2$), 46.23 (CH$_3$), 38.42, 37.56 (CH$_2$), 37.04, 36.31 (CH$_2$), 34.93, 32.97 (CH$_2$), 25.68, 25.52 (CH$_2$), 24.72, 24.63 (CH$_2$), 23.56 (CH$_3$) ppm.

Example 12

Synthesis of 1-(2,8)-dimethyl-1-thia-3,8-diaza-spiro [4.5]dec-3-yl)-4-(1H-indol-3-yl)-ethan-1-one (AF726)

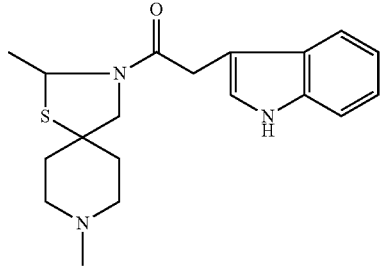 [SMILES: CC1SC2(CCN(C)CC2)CN1C(=O)Cc1c[nH]c2ccccc12]

To a stirred solution of 2,8-dimethyl-1-thia-3,8-diaza-spiro[4.5]decane (Example 1) (0.97 g, 52 mmol) in dichloromethane (100 ml) at room temperature was added dicyclohexylcarbodiimide (DCC) (1.44 g, 6.98 mmol) followed by addition of 3-indoleacetic acid (1.09 g, 6.22 mmol). The resulting solution was stirred at room temperature overnight. During the reaction a white solid precipitated. After filtration the solvent was evaporated and the crude product was purified by flash chromatography (silica, $CH_2Cl_2$/MeOH/$NH_4OH$ 90/10/1) to give the title compound (600 mg) as a solid. $^1H$ NMR ($CDCl_3$, 300 MHz) δ 8.71, 8.66 (2 br s, 1H, NH-indole), 7.62, 7.59 (2d, J=7.90 and J=8.39 Hz, 1H, CHC arom), 7.35 (m, 1H, CHC arom), 7.22-7.08 (m, 1H, 2CH arom), 7.03 (br s, 1H, CHNH arom), 5.53, 5.33 (2q, J=6.12 and J=6.22 Hz, 1H, CHCH$_3$), 4.69, 3.88 (2d, J=12.15 and J=11.20 Hz, 1H, CHHNCO), 3.49 and 3.81 (2s, 2H, C(O)CH$_2$), 3.36, 3.13 (2d, J=11.41 and J=12.19 Hz, 1H, CHHNCO), 2.8-2.5 (m, 1H), 2.5-2.05 (m, 2H), 2.25 and 2.19 (2s, 3H, NCH$_3$), 2.05-1.85 (m, 2H), 1.85-1.6 (m, 1H), 1.52, 1.48 (2d, J=6.15 and J=6.30 Hz, 3H, CH$_3$—CH), 1.45-1.35 (m, 1H), 1.35-1.15 (m, 1H) ppm; $^{13}C$ NMR ($CDCl_3$, 300 MHz) δ 169.6 (C), 136.43 (C), 127.19 (C), 122.98, 122.82 (CH), 122.43 (CH), 119.88, 119.81 (CH), 118.79, 118.67 (CH), 111.52 (CH), 108.55 (C), 58.06, 57.58 (CH), 55.66 (C), 54.66, 54.15 (CH$_2$), 53.20, 52.76 (CH$_2$), 46.27, 46.11 (CH$_3$), 38.45, 37.13 (CH$_2$), 36.95, 36.13 (CH$_2$), 33.96 (CH$_2$), 31.37 (CH$_2$), 25.75, 23.33 (CH$_3$) ppm.

Example 13

Synthesis of (E)-1-(2,8-dimethyl-1-thia-3,8-diaza-spiro[4.5]dec-3-yl)-3-(1H-indol-3-yl)-propenone (AF727)

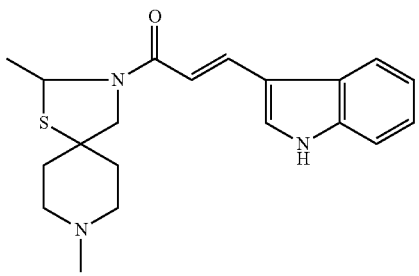 [SMILES: CC1SC2(CCN(C)CC2)CN1C(=O)/C=C/c1c[nH]c2ccccc12]

To a stirred solution of 2,8-dimethyl-1-thia-3,8-diaza-spiro[4.5]decane (Example 1) (0.83 g, 44 mmol) in dichloromethane (85 ml) at room temperature was added dicyclohexylcarbodiimide (DCC) (1.23 g, 5.9 mmol) followed by addition of trans-3-indoleaceticrylic acid (1.0 g, 5.3 mmol). The resulting solution was stirred at room temperature overnight. During the reaction a white solid has precipitated. After filtration the solvent was evaporated and the crude product was purified by flash chromatography (silica, $CH_2Cl_2$/MeOH/$NH_4OH$ 90/10/1) to give the title compound (600 mg) as a solid. $^1H$ NMR (1,1,2,2-Dichloroethane-d$_2$, 300 MHz, 100° C.) δ 8.56 (br s, 1H, NH-indole), 7.94 (d, J=15.3 Hz, 1H, HC=C), 7.83 (m, 1H, CHC arom), 7.46 (br s, 1H, CHC arom), 7.42 (m, 1H, CH), 7.26 (m, 2H, 2CH arom), 6.71 (d, J=15.3 Hz, 1H, C=CH), 5.65 (q, J=6.12 Hz, 1H, CHCH$_3$), 4.38 (d, J=11.75 Hz, 1H, CHHNCO), 3.50 (d, J=11.84 Hz, 1H, CHHNCO), 3.1-2.8 (m, 2H), 2.8-2.6 (m, 1H), 2.6-2.3 (m, 2H), 2.46 (s, 3H, NCH$_3$), 2.2-1.9 (m, 2H), 1.9-1.8 (m, 1H), 1.64 (d, J=6.21 Hz, 3H, CH$_3$—CH) ppm; MS (EI+) m/z 355 (M+), 322, 185, 170.

Example 14

Synthesis of 1-(2,8-dimethyl-1-oxa-3,8-diazaspiro[4.5]dec-3-yl)-3-(1H-indol-3-yl)-propan-1-one (AF711)

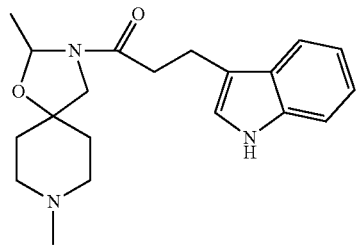 [SMILES: CC1OC2(CCN(C)CC2)CN1C(=O)CCc1c[nH]c2ccccc12]

To a stirred solution of 2,8-dimethyl-1-oxa-3,8-diaza-spiro[4.5]decane (991.2 mg, 5.8 mmol) in dichloromethane (110 ml) at room temperature were added dicyclohexylcarbodiimide (1.61 g, 7.8 mmol) and 3-indolepropionic acid (1.43 g, 7.6 mmol). The resulting solution was stirred at room temperature overnight. A white solid precipitated during the reaction. After filtration the solvent was evaporated and the crude product was purified by flash chromatography (silica, $CH_2Cl_2$/EtOH/$NH_4OH$ 90/10/1). After evaporation and drying under vacuum, AF711 (716 mg, 99.6% chemical purity) was obtained as a white solid. $^1H$ NMR ($CDCl_3$, 500 MHz) δ 8.50, 8.46 (2 br s, 1H, NH indole), 7.61 (d, J=7.55 Hz, 1H, CHC arom), 7.33 (d, J=7.85 Hz, 1H, CHCNH arom), 7.18 (app t, J=7.24, 7.85 Hz, 1H, CHCHC arom), 7.11 (app t, J=7.55, 7.24 Hz, 1H, CHCHC arom), 7.02 (d, J=1.86 Hz, 1H, CHNH indole), 5.32, 5.15 (2q, J=5.09 and J=5.16 Hz, 1H, CHCH$_3$), 3.99, 3.22 (2d, J=11 and J=9.5 Hz, 1H, CHHNCO), 3.19 (m, 1H), 3.13-3.08 (m, 1H), 3.03, 2.97 (2d, J=9.5 and J=11 Hz, 1H, CHHNCO), 2.72-2.60 (m, 2H), 2.51-2.20 (m, 4H), 2.25, 2.23 (2s, 3H, NCH$_3$), 1.78-1.64 (m, 2H), 1.43, 1.31 (2d, J=5.15 and J=5.15 Hz, 3H, CH$_3$CH), 1.39, 1.28 (2m, 1H), 1.14 (m, 1H) ppm; $^{13}C$ NMR ($CDCl_3$, 500 MHz) δ 170.50, 169.85 (C), 136.30, 136.25 (C), 127.07, 126.99 (C), 121.93 (CH), 121.85 (CH), 119.24 (CH), 118.55, 118.52 (CH), 114.73 (C), 111.20, 111.12 (CH), 84.69, 84.06 (CH), 77.98 (C), 54.18 (CH$_2$), 52.18 (CH$_2$), 51.86 (CH$_2$), 45.89, 45.83 (CH$_3$), 36.38 (CH$_2$), 34.98 (CH$_2$), 32.99, 32.41 (CH$_2$), 22.70, 20.50 (CH$_3$), 20.96, 20.73 (CH$_2$) ppm.

Example 15

Chiral separation of AF711A and AF711B

The separation of AF711 to its enantiomers was done by HPLC on a semipreparative column. 200 µl of solution of AF711 in methanol (50 mg/ml) was injected into the column and eluted. Following elution, the eluent was evaporated to dryness.
HPLC: Merck-Hitachi model L-62000A
Detector: Merck-Hitachi model L-4250
Column: Chiralcel OJ-H, 250×10 mm
Flow rate: 4 ml/min
Column Temp: room temperature
Mobile phase: Hexane/Etanol/Methanol 95:1:4
Concentration: 50 mg/ml
UV Detection: 300 nm
First eluting enantiomer (AF711A): 99% ee (assumed to be the (−) enantiomer)
Second eluting enantiomer (AF711B): 99% ee, specific rotation [α]=+73.5° (C=0.365, Methanol)

Example 16

Synthesis of 1-(2,8-dimethyl-1-oxa-3,8-diaza-spiro[4.5]dec-3-yl)-2-propyl-pentan-1-one (AF712)

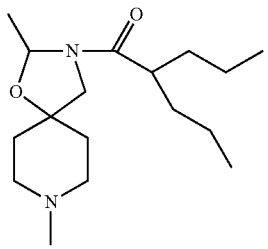 [SMILES: CCCC(CCC)C(=O)N1CC2(CCN(C)CC2)OC1C]

2,8-Dimethyl-1-oxa-3,8-diaza-spiro[4.5]decane (1.52 g, 8.95 mmol) was dissolved in dry dichloromethane (5 ml) under an argon atmosphere. Distilled triethylamine (1.87 ml, 13.42 mmol) was added and the resulting solution was cooled to 0° C. Valproyl chloride (1.46 g, 8.95 mmol) was added dropwise with a syringe. The reaction flask was allowed to warm to room temperature with stirring, and a white solid started to precipitate. After 4 h of stirring, dichloromethane (100 ml) was added and the resulting solution was washed with water (10 ml). The two phases were separated and the aqueous phase was extracted with dichloromethane (2×50 ml). The combined organic phase was dried with anhydrous sodium sulfate, filtered and evaporated under reduced pressure. The residue was purified by flash chromatography (silica, $CH_2Cl_2$/EtOH/$NH_4OH$ 130/10/1) to give AF712 (389 mg, 98.7% chemical purity) as a yellow powder. $^1$H NMR. ($CDCl_3$, 300 MHz) δ 5.43 (q, J=5.2 Hz, 1H, CHCH$_3$), 4.13, 3.63 (2d, J=11.35 and J=9.6 Hz, 1H, CHHNCO), 3.22, 3.00 (2d, J=9.6 and J=11.35 Hz, 1H, CHHNCO), 2.56-2.38 (m, 5H), 2.30, 2.29 (2s, 3H, NCH$_3$), 1.84-1.53 (3m, 6H), 1.44, 1.43 (2d, J=5.2 Hz, 3H, CH$_3$CH), 1.4-1.19 (m, 6H), 0.90 (app t, J=7.11 Hz, 6H, CH$_3$CH$_2$) ppm; $^{13}$C NMR. ($CDCl_3$, 300 MHz) δ 173.92, 173.68 (C), 84.75, 84.20 (CH), 78.32, 78.09 (C), 54.24 (CH$_2$), 52.34 (CH$_2$), 52.02 (CH$_2$), 46.03 (CH$_3$), 44.34, 43.64 (CH), 35.63 (CH$_2$), 35.05 (CH$_2$), 34.92 (CH$_2$), 32.83 (CH$_2$), 23.52, 20.91 (CH$_3$), 20.59 (CH$_2$), 20.43 (CH$_2$), 14.30 (CH$_3$), 14.16 (CH$_3$) ppm.

Example 17

Synthesis of 3-(4-fluorobenzenesulfonyl)-2,8-dimethyl-1-oxa-3,8-diazaspiro[4.5]-decane (AF715)

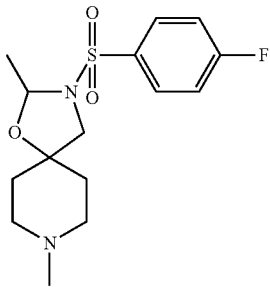 [SMILES: CC1OC2(CCN(C)CC2)CN1S(=O)(=O)c1ccc(F)cc1]

2,8-Dimethyl-1-oxa-3,8-diaza-spiro[4.5]decane (1.42 g, 8.38 mmol) was dissolved in dry dichloromethane (5 ml) under argon atmosphere. Distilled triethylamine (1.75 ml, 12.57 mmol) was added and the resulted solution was cooled to 0° C. p-Fluorobenzenesulfonyl chloride (1.63 gr, 8.37 mmol) was added and the reaction flask was allowed to warm to room temperature with stirring, and a white solid started to precipitate. After 30 min of stirring, dichloromethane (90 ml) was added and the resulting solution was washed with water (2×10 ml). The organic phase was dried with anhydrous sodium sulfate, filtered and evaporated. The residue was purified by flash chromatography (silica, $CH_2Cl_2$/EtOH/$NH_4OH$ 140/10/1) to give AF715 (1.23 g, 98.7% chemical purity) as an off-white powder. $^1$H NMR. ($CDCl_3$, 500 MHz) δ 7.89-7.87 (m, 2H, CHCSO$_2$), 7.27-7.22 (m, 2H, CHCF), 5.05 (q, J=5.23, 1H, CHCH$_3$), 3.33 (d, J=10.26 Hz, 1H, CHHNS), 3.19 (d, J=10.26 Hz, 1H, CHHNS), 2.52-2.42 (m, 114), 2.34-2.25 (m, 2H), 2.23 (s, 3H, NCH$_3$), 2.18-2.09 (m, 1H), 1.77-1.72 (m, 2H), 1.52 (d, J=5.23 Hz, 3H, CH$_3$CH), 1.25-1.18 (m, 1H), 1.10-1.03 (m, 1H) ppm; $^{13}$C NMR ($CDCl_3$, 500 MHz) δ 166.45 and 164.42 (C), 134.0 (C), 130.37 (CH), 130.29 (CH), 116.68 (CH), 116.50 (CH), 86.95 (CH), 66.30 (C), 55.48 (CH$_2$), 52.57 (CH$_2$), 52.11 (CH$_2$), 46.04 (CH$_3$), 35.64 (CH$_2$), 32.84 (CH$_2$), 22.95 (CH$_3$) ppm.

Example 18

Synthesis of 1-(2,8-dimethyl-1-oxa-4,8-diazaspiro[4.5]dec-4-yl)-3-(1H-indol-3-yl)-propan-1-one (AF706)

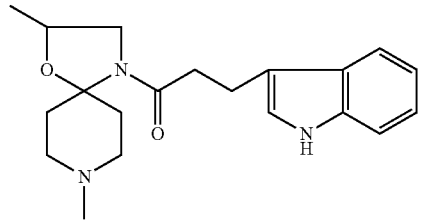 [SMILES: CC1CN(C(=O)CCc2c[nH]c3ccccc23)C2(CCN(C)CC2)O1]

A solution of 2,8-dimethyl-1-oxa-4,8-diazaspiro[4.5]decane (1.09 g, 6.41 mmol), 3-indolpropionic acid (1.57 g, 8.3 mmol), dicyclohexylcarbodiimide (DCC, 1.78 g, 8.65 mmol) and dimethylaminopyridine (DMAP, 0.78 g, 6.41 mol) in dichloromethane (100 ml) was stirred at room temperature for 4 days. The precipitate was removed by filtration and the solvent was evaporated. Flash chromatography (silica, $CH_2Cl_2$/i-PrOH/$NH_4OH$ 85/15/1) gave the title compound that was triturated in ether. The obtained white solid (AF706), 1.1 gr (99.4% chemical purity), was filtered and dried. $^1$H-NMR ($CDCl_3$, 300 MHz) δ 8.15 (br NH), 7.63 (d, J=7.76 Hz, 1H, ArH), 7.38 (d, J=7.98 Hz, 1H, ArH), 7.23 (dt, J=1.12, 7.56 Hz, 1H, ArH), 7.13 (dt, J=1.07, 7.44 Hz, 1H, ArH), 7.08 (d, J=2.15 Hz, 1H, NCHC), 4.05 (m, 1H, OCH), 3.53 (dd, J=9.0, 5.5 Hz, 1H, NCHH), 3.13 (m, 3H), 2.96 (t, J=9.2 Hz, 1H), 2.80-2.70 (m, 3H), 2.61-2.70 ((m, 2H), 2.23-2.34 (m, 2H, CH$_2$-piperidine), 2.31 (s, 3H, NCH$_3$), 1.37 (m, 1H, CH-piperidine), 1.33 (m, 1H, CH-piperidine), 1.25 (d, J=6.0 Hz, 3H, CH$_3$) ppm; $^{13}$C-NMR ($CDCl_3$, 300 MHz) δ 169.66 (C), 136.52 (C), 122.49 (CH), 121.90 (CH), 119.24 (CH), 118.78 (CH), 115.18 (C), 111.41 (CH), 94.16 (C), 69.92 (CH), 53.25 (CH$_2$), 52.84 (CH$_2$), 52.70 (CH$_2$), 45.99 (CH$_3$), 37.52 (CH$_2$), 33.66 (CH$_2$), 30.90 (CH$_2$), 20.73 (CH$_2$), 18.26 (CH$_3$) ppm.

Example 19

Synthesis of 1-(2,8-dimethyl-1-oxa-4,8-diaza-spiro[4.5]dec-4-yl)-2-propyl-pentan-1-one (AF713)

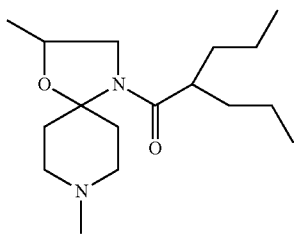 [SMILES: CCCC(CCC)C(=O)N1CC(C)OC12CCN(C)CC2]

To a cold (0° C., ice-water bath) solution of sodium hydride (60%, 0.6 g, 15 mmol) in THF (60 ml) was added 2,8-dimethyl-1-oxa-4,8-diazaspiro[4.5]decane (2.44 g, 14.3 mmol) under an argon atmosphere. The cooling bath was removed and the reaction mixture was stirred at room temperature for 30 min. Valproyl chloride (2.36 g, 14.5 mmol) was added and the reaction mixture was left at room temperature under argon atmosphere for 2.5 h with stirring. The reaction mixture was filtered through a short pad of silica. The silica was washed with THF (3×150 ml), the filtrates were combined and evaporated. Flash chromatography (silica, $CH_2Cl_2$/EtOH/$NH_4OH$ 100/10/1) gave the title compound as a yellow-brown solid. The solid was dissolved in dichloromethane (150 ml) and charcoal was added to the stirred solution. Filtration and evaporation gave off-white AF713 (1.4 g, 97.2% chemical purity). $^1$H-NMR ($CDCl_3$, 300 MHz) δ 4.1-4.2 (m, 1H, OCH), 3.7-3.8 (m, 1H), 3.0-3.2 (m, 2H), 2.7-2.8 (m, 3H), 2.3-2.5 (m, 3H), 2.3 (s, 3H, $NCH_3$), 1.55-1.67 (m, 2H), 1.4-1.52 (m, 1H), 1.26 (d, J=6 Hz, 3H, $CH_3$), 1.2-1.4 (m, 6H), 0.89 (br t, J=7.03 Hz, 6H, $2CH_3$) ppm; $^{13}$C-NMR ($CDCl_3$, 300 MHz) δ 173.14 (C), 94.22 (C), 69.65 (CH), 53.41 ($CH_2$), 52.46 ($CH_2$), 52.30 ($CH_2$), 45.35 ($CH_2$), 45.06 ($CH_2$), 35.35 ($CH_2$), 35.21 ($CH_2$), 32.93 ($CH_2$), 30.27 ($CH_2$), 20.79 ($CH_2$), 20.73 ($CH_2$), 18.14 ($CH_3$), 14.33 ($CH_3$), 14.27 ($CH_3$) ppm; FTIR(HATR) 1627 $cm^{-1}$.

Example 20

Synthesis of 4-(4-fluoro-benzenesulfonyl)-2,8-dimethyl-1-oxa-4,8-diaza-spiro[4.5]-decane (AF7141)

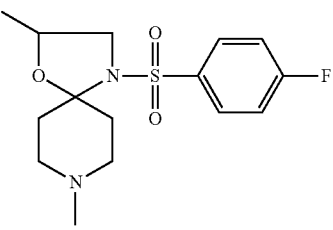 [SMILES: CC1CN(S(=O)(=O)c2ccc(F)cc2)C2(CCN(C)CC2)O1]

Into a cold (0° C., ice-water bath) solution of sodium hydride (60%, 0.6 g, 15 mmol) in THF (60 ml) was added 2,8-dimethyl-1-oxa-4,8-diazaspiro[4.5]decane (2.49 g, 14.6 mmol) under an argon atmosphere. The cooling bath was removed and the reaction mixture was stirred at room temperature for 40 min. 4-Fluorobenzensulfonyl chloride (2.84 gr, 14.6 mmol) was added and the reaction mixture was left at room temperature under argon atmosphere overnight with stirring. The reaction mixture was filtered through a short pad of silica, which was washed with tetrahydrofurn (THF, 2×150 ml). The filtrates were combined and evaporated. Flash chromatography (silica, $CH_2Cl_2$/EtOH/$NH_4OH$ 100/10/1) gave the title compound as a yellow-brown solid. The solid was recrystallized from hot i-PrOH. AF714 was obtained as a white solid (1.3 g, 99.8% chemical purity). $^1$H-NMR ($CDCl_3$, 300 MHz) δ 7.88 (m, 2H, 2H-Ar), 7.20 (m, 2H, 2H-Ar), 4.21 (m, 1H, OCH), 3.69 (dd, J=5.4, 8.4 Hz, 1H, NCHH), 2.91 (t, J=8.8 Hz, 1H, NCHH), 2.72 (m, 2H, $CH_2$-piperidine), 2.63 (m, 1H, CH-piperidine), 2.43 (m, 1H, CH-piperidine), 2.28 (s, 3H, $NCH_3$), 2.25 (m, 2H, $CH_2$-piperidine), 1.72 (m, 1H, CH-piperidine), 1.43 (m, 1H, CH-piperidine), 1.28 (d, J=6 Hz, 3H, $CH_3$); $^{13}$C-NMR ($CDCl_3$, 300 MHz) δ 166.58 and 163.20 (C), 137.02 (C), 129.95 (C), 129.83 (C), 116.34 (C), 116.04 (C), 96.29 (C), 70.42 (CH), 53.49 ($CH_2$), 52.96 ($CH_2$), 52.79 ($CH_2$), 45.85 ($CH_3$), 35.88 ($CH_2$), 34.89 ($CH_2$), 18.08 ($CH_2$) ppm.

Example 21

Synthesis of 1',4-dimethyl-6-(3-indolpropionyl)-spiro-(3-oxa-6-aza-bicyclo[3.1.0]-hexane-2,4'-piperidine) (AF718C)

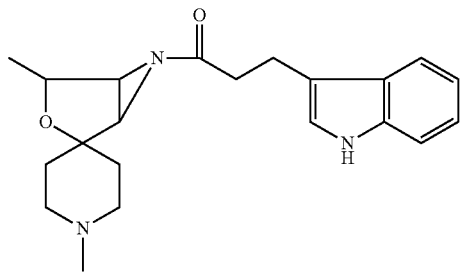 [SMILES: CC1OC2(CCN(C)CC2)C2C1N2C(=O)CCc1c[nH]c2ccccc12]

A solution of 3-indolepropionic acid (1.63 g, 8.6 mmol) and dicyclohexyl-carbodiimide (DCC, 1.86 g, 9.06 mmol) in dichloromethane (50 ml) was stirred at room temperature for 15 min. 1-Hydroxybenzotriazole (HOBT, 1.22 gr 9.06 mmol) was added and the stirring was continued for an additional 30 min. 1',4-Dimethylspiro-3-oxa-6-azabicyclo[3.1.0]hexane-2,4'-piperidine (1.57 g, 8.6 mmol) was added and the reaction mixture was stirred overnight at room temperature. Dichloromethane (100 ml) was added and reaction mixture was washed with water (2×20 ml). The organic fractions were combined, dried and concentrated under reduced pressure. Flash chromatography (silica, $CH_2Cl_2$/EtOH/$NH_4OH$ 100/20/1) of the residue gave AF718C (200 mg, 99.3% chemical purity) as a white solid. $^1$H-NMR ($CDCl_3$, 300 MHz) δ 8.08 (br NH), 59 (d, J=7.72 Hz, 11-1, ArH), 7.36 (d, J=7.91 Hz, 1H, ArH), 7.21 (dt, J=1.19, 7.45 Hz, 1H, ArH), 7.13 (dt, J=1.13, 7.40 Hz, 1H, ArH), 6.98 (d, J=2.24 Hz, 1H, NCHC), 4.15 (q, J=6.77 Hz, 1H, OCH), 3.12 (t, J=7.25 Hz, 2H, $CH_2$), 2.92 (d, J=4.7 Hz, 1H, NCH), 2.85 (d, J=4.7 Hz, 1H, NCH), 2.85-2.74 (m, 2H, $CH_2$), 2.4-2.2 (m, 4H, $2CH_2$-piperidine), 2.25 (s, 3H, $NCH_3$), 1.76-1.67 (m, 2H, $CH_2$-piperidine), 1.66-1.56 (m, 2H, $CH_2$-piperidine), 1.12 (d, J=6.8 Hz, 3H, $CH_3$) ppm; $^{13}$C-NMR ($CDCl_3$, 300 MHz) δ 184.40 (C), 136.26 (C), 122.16 (CH), 121.67 (CH), 119.53 (CH), 118.65 (CH), 114.93 (C), 111.23 (CH), 78.69 (C), 74.50 (CH), 53.08 ($CH_2$), 52.08 ($CH_2$), 47.14 (CH), 46.25 (CH), 45.95 ($CH_3$), 37.90 (CH$_2$), 36.02 (CH$_2$), 33.39 (CH$_2$), 20.93 (CH$_2$), 20.77 (CH$_3$) ppm; FT-IR(HATR) 1676 cm$^{-1}$; MS (CI) 354 (M+1) for C$_{21}$H$_{27}$N$_3$O$_2$.

Example 22

Synthesis of 1',4-dimethyl-6-[3-(4-fluorobenzenesulfonyl)]-spiro-(3-oxa-6-aza-bicyclo[3.1.0]hexane-2,4'-piperidine) (AF721)

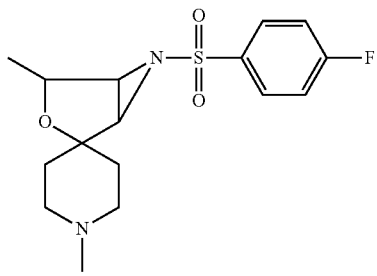 [SMILES: CC1OC2(CCN(C)CC2)C2C1N2S(=O)(=O)c1ccc(F)cc1]

A solution of 4-fluorobenzenesulfonyl chloride (1.04 g, 5.3 mmol) in dry dichloromethane (5 ml) was added to a solution of amine [see synthesis of AF718C part (a), 0.97 g, 5.3 mmol] and dry triethylamine (1.1 ml, 8 mmol) in dry dichloromethane (12 ml). The reaction mixture was stirred overnight at room temperature. Dichloromethane (50 ml) was added and the reaction mixture was washed with water (10 ml). The organic phase was dried and concentrated under reduced pressure. Flash chromatography of the residue gave AF721 (oil, 0.8 g). $^1$H-NMR (CDCl$_3$, 300 MHz) δ 8.01-7.95 (m, 2H, 2CH), 7.28-7.16 (m, 2H, 2CH), 4.24 (q, J=6.83 Hz, 1H, OCH), 3.54-3.48 (two d, J=5.38 and J=5.38 Hz, 2H, 2CH), 2.53-2.3 (m, 4H), 2.23 (s, 3H, NCH$_3$), 2.16-1.73 (m, 4H), 1.25 d, J=6.84 Hz, 3H, CH$_3$) ppm; $^{13}$C-NMR (CDCl$_3$, 300 MHz) δ 167.5 and 164.1 (CF), 134.2 (C), 130.7 (CH), 130.6 (CH), 116.6 (CH), 116.3 (CH), 79.6 (C), 75.0 (CH), 52.8 (CH$_2$), 52.2 (CH$_2$), 50.9 (CH), 49.9 (CH), 46.0 (CH$_3$), 36.3 (CH$_2$), 33.1 (CH$_2$), 20.9 (CH$_3$) ppm.

Example 23

Synthesis of 1-(2,8-Dimethyl-1-thia-3,8-diazaspiro[4.5]dec-3-yl)-3-(1-methyl-indol-3-yl)propan-1-one (AF732)

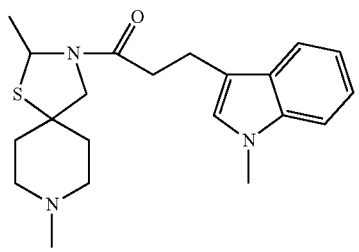 [SMILES: CC1SC2(CCN(C)CC2)CN1C(=O)CCc1cn(C)c2ccccc12]

To a solution of dicyclohexylcarbodiimide (DCC) (1.3 g, 6.3 mmol) in dichloromethane (50 ml) at room temperature was added 3-(1-methyl-indole-3-yl)propanoic acid (1.18 g, 5.8 mmol) and a solution of 2,8-dimethyl-1-thia-3,8-diazaspiro[4.5]decane (1.2 g, 6.4 mmol) in dichloromethane (50 ml). The resulting solution was stirred at room temperature for 48 h. During the reaction a white solid precipitated. After filtration, the solvent was evaporated and the crude product was purified by flash chromatography (silica, CH$_2$Cl$_2$/EtOH/NH$_4$OH 100/10/1) to give the title compound (0.7 g) as a colorless oil. $^1$H NMR (CDCl$_3$, 300 MHz) δ 7.60 (d, J=7.82 Hz, 1H, CHC arom), 7.35-7.2 (m, 2H, 2CHC arom), 7.23 (dt, J=1.06, 7.45 Hz, 1H, CHCH arom), 6.90 (s, 1H, CHNH arom), 5.54, 5.07 (2q, J=6.16 and J=6.25 Hz, 1H, CHCH$_3$), 4.63, 3.68 (2d, J=12.0 and J=11.5 Hz, 1H, CHHNCO), 3.75, 3.74 (2s, 3H, NCH$_3$), 3.32 (d, J=11.5 Hz, 0.6H, CHHNCO), 3.17-3.05 (m, 2.4H), 2.8-2.4 (m), 2.68 [t, J=7.6 Hz, C(O)CH$_2$], 2.28, 2.26 (2s, 3H, NCH$_3$), 2.3-2.2 (m), 2.1-2.0 (m), 2.0-1.8 (m), 1.7-1.4 (m), 1.48, 1.43 (2d, J=6.18 and J=6.26 Hz, 3H, CH$_3$—CH) ppm; $^{13}$C NMR (CDCl$_3$, 300 MHz) δ 170.6 (C), 137.1 (C), 126.8 (C), 126.7 (CH), 121.8 (CH), 119.0 (CH), 118.9 (CH), 113.7 (C), 109.4 (CH), 59.0 (C), 57.5, 57.2 (CH), 54.6, 54.2 (CH$_2$), 53.2, 52.9 (CH$_2$), 46.3, 46.2 (CH$_3$), 38.1, 37.4 (CH$_2$), 36.9, 36.6 (CH$_2$), 36.4, 34.7 (CH$_2$), 32.7 (CH$_3$), 25.5, 23.5 (CH$_3$), 21.0, 20.9 (CH$_2$) ppm.

Example 24

Synthesis of N-(2,8-dimethyl-1-oxa-8-aza-spiro[4.5]dec-3-yl)-3-(1H-indol-3-yl)-propionamide (AF730)

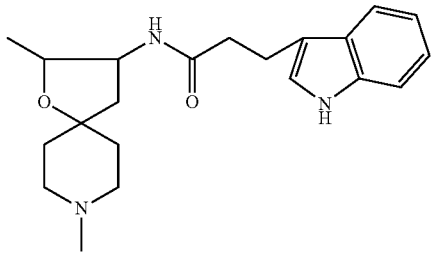 [SMILES: CC1OC2(CCN(C)CC2)CC1NC(=O)CCc1c[nH]c2ccccc12]

Synthesis of 2,8-Dimethyl-1-oxa-8-aza-spiro[4.5]dec-3-ylamine: A solution of 2,8-Dimethyl-1-oxa-8-aza-spiro[4.5]decan-3-one oxime (1.24 g, 6.3 mmol, prepared according to the procedure of Tsukamoto et. al. *Chem. Pharma. Bull.* 1995, 43, 842-852) in dry THF (30 ml) was added dropwise to a suspension of lithium aluminium hydride (1.13 g, 30 mmol) and aluminium chloride (0.2 g, 1.5 mmol) in dry THF (50 ml). The reaction mixture was stirred for 10 h at room temperature. The reaction mixture was cooled (ice) and the reaction quenched by addition of water (3 ml), 15% aqueous NaOH (3 ml) and water (7 ml). The solid was filtered off over celite and the THF filtrate was concentrated in vacuo. The residual oil was dissolved in dichloromethane (200 ml) and the solution was dried with sodium sulfate. The solvent was removed and the crude amine was taken to the next step.

To a stirred solution of dicyclohexylcarbodiimide (DCC) (1.49 g, 7 mmol) in dichloromethane (100 ml) at room temperature was added a solution of 2,8-Dimethyl-1-oxa-8-aza-spiro[4.5]dec-3-ylamine (all the of the compound obtained from the previous step) in dichloromethane (20 ml), followed by addition of 3-indolepropionic acid (1.3 g, 6.9 mmol). The reaction mixture was stirred at room temperature overnight. During the reaction a white solid precipitated. After filtration the solvent was evaporated and the crude product was purified by flash chromatography (silica, gradient from CH$_2$Cl$_2$/MeOH/NH$_4$OH 140/10/1 to CH$_2$Cl$_2$/MeOH/NH$_4$OH 100/10/1) to give white solid of AF730 as a mixture of two geometrical isomers (isomer I/isomer II 1:2). $^1$H NMR (CDCl$_3$, 300 MHz) δ 8.07 (br s, 1H, NH-indole), 7.61 (d, J=7.81 Hz, 1H, CHC arom), 7.36 (d, J=8.0 Hz, 1H, CHC arom, isomer II), 7.35 (d, J=7.9 Hz, 1H, CHC arom, isomer I), 7.20 (m, 1H, CHCH arom), 7.15 (m, 1H, CHCHarom), 7.02 (m, 1H, CHNH arom), 5.36 (d, J=8.85 Hz, 1H, NH isomer I), 5.18 (d, J.=8.0 Hz, 1H, NH isomer II), 4.35 (m, 1H, CH isomer I), 4.04 (m, 1H, CH isomer II), 3.93 (m, 1H, CHCH$_3$ isomer I), 3.48 (m, 1H, CHCH$_3$ isomer II), 3.13 (t, J=7.0 Hz, 2H, COCH$_2$CH$_2$), 2.58 (m, 2H, COCH$_2$), 2.4 (m, 2H, CH$_2$), 2.29 (m, 2H, CH$_2$), 2.25 (s, 3H, NCH$_3$ isomer II), 2.23 (s, 3H, NCH$_3$ isomer I), 2.10 (dd, J=12.9, 8.2 Hz, 1H, CHHCH isomer II), 1.96 (dd, J=13.6, 7.1 Hz, 1H, CHHCH isomer I), 1.7-1.4 (2m), 1.4-1.2 (2m), 1.15 (d, J=6.1 Hz, 3H, CH$_3$—CH isomer II), 0.97 (d, J=6.3 Hz, 3H, CH$_3$—CH isomer I) ppm; $^{13}$C NMR (CDCl$_3$, 300 MHz) δ 172.9, 172.5 (C), 136.6, 136.5 (C), 127.2, 127.1 (C), 122.2, 122.1 (CH), 119.6, 119.5 (CH), 118.8 (CH), 114.6, 114.5 (C), 111.6, 111.5 (CH), 78.2, 74.5 (CH), 55.5 (CH), 53.0 (C), 52.9, 52.7 (CH$_2$), 46.6, 46.2 (CH$_3$), 38.7, 38.5 (CH$_2$), 37.7, 37.6 (CH$_2$), 21.8, 21.7 (CH$_2$), 19.7, 15.0 (CH$_3$) ppm.

The geometrical isomers (200 mg) were separated by flash chromatography in a Combi-Flash Companion system (Isco, Inc) (HP 40-gold silica column, linear gradient CH$_2$Cl$_2$/MeOH/NH$_4$OH 120/10/1 to CH$_2$Cl$_2$/MeOH/NH$_4$OH 90/10/1). AF730 I (less polar isomer): $^1$H NMR (CDCl$_3$, 300 MHz) δ 8.09 (br s, 1H, NH-indole), 7.61 (d, J=7.80 Hz, 1H, CHC arom), 7.35 (d, J=8.0 Hz, 1H, CHC arom), 7.19 (dt, J=1.1, 7.4 Hz, 1H, CHCH arom), 7.12 (dt, J=1.01, 7.4 Hz, 1H, CHCHarom), 7.03 (d, J=2.2 Hz, 1H, CHNH arom), 5.36 (d, J=8.6 Hz, 1H, M-1), 4.35 (m, 1H, CH), 3.93 (dq, J=6.3, 6.3 Hz, 1H, CHCH$_3$), 3.13 (t, J=7.1 Hz, 2H, COCH$_2$CH$_2$), 2.58 (m, 2H, COCH$_2$), 2.5-2.1 (m, 4H, 2CH$_2$), 2.24 (s, 3H, NCH$_3$), 1.96 (dd, J=13.6, 7.1 Hz, 1H, CHHCH), 1.7-1.4 (2m, 2H), 1.4-1.3 (m, 2H), 1.31 (dd, J=13.6, 2.7 Hz, 1H, CHHCH), 0.97 (d, J=6.3 Hz, 3H, CH$_3$—CH) ppm. AF730 II (more polar isomer): $^1$H NMR (CDCl$_3$, 300 MHz) δ 8.1 (br s, 1H, NH-indole), 7.60 (d, J=7.82 Hz, 1H, CHC arom), 7.36 (d, J=8.0 Hz, 1H, CHC arom), 7.20 (dt, J=1.1, 7.5 Hz, 1H, CHCH arom), 7.12 (dt, J=1.1, 7.4 Hz, 1H, CHCH arom), 7.01 (d, J=2.2 Hz, 1H, CHNH arom), 5.19 (d, J=8.30 Hz, 1H, NH), 4.03 (m, 1H, CH), 3.46 (m, 1H, CHCH$_3$), 3.13 (t, J=7.1 Hz, 2H, COCH$_2$CH$_2$), 2.57 (t, J=7.1 Hz, 2H, COCH$_2$), 2.5-2.3 (m, 2H, CH$_2$), 2.3-2.1 (m, 2H, CH$_2$), 2.24 (s, 3H, NCH$_3$), 2.10 (dd, J=12.9, 8.2 Hz, 1H, CHHCH), 1.7-1.4 (2m, 4H), 1.26 (dd, J=12.7, 7.6 Hz, 1H, CHHCH), 1.15 (d, J=6.1 Hz, 3H, CH$_3$—CH) ppm.

Example 25

N-(2,8-Dimethyl-1-thia-8-aza-spiro[4.5]dec-3-yl)-3-(1H-indol-3-yl)-propionamide (AF731)

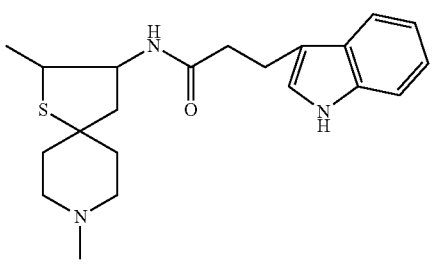 [SMILES: CC1SC2(CCN(C)CC2)CC1NC(=O)CCc1c[nH]c2ccccc12]

(a) Synthesis of 2,8-dimethyl-1-thia-8-azaspiro[4.5]decane-3-one. In a three-necked round bottom flask fitted with a thermometer, dropping funnel and calcium chloride drying tube, 60% sodium hydride in mineral oil (8.74 g, 0.218 mol) and dry ether (300 ml) were placed. To this stirred and cooled suspension a solution of ethyl thiolactate (28.4 g, 95%, 0.200 mol) in dry ether (100 ml) was added at 5-10° C., followed by slow addition of methanol (100 ml) at the same temperature. Then the reaction mixture was stirred at room temperature for one hour. The solvents were removed under reduced pressure and to the residue dry dimethylsulfoxide (170 ml) was added. The obtained solution was cooled to 15° C. and ethyl(1-methyl-4-piperidinylidene) acetate (40 g, 0.22 mol) was added. The reaction mixture was stirred at room temperature for two days, then poured into ice-cold water (600 ml). The reaction mixture was then acidified with concentrated hydrochloric acid, and then made basic (pH 8) with sodium bicarbonate. The reaction mixture was then extracted with dichloromethane (4×450 ml) and the combined extracts were washed with brine (2×400 ml), dried (MgSO$_4$) and the solvents removed to give an oil (59.40 g) which contained some dimethylsulfoxide. To part of the above product (27.6 g), hydrochloric acid (1.3 N, 200 ml) was added, and the solution obtained was refluxed for 11 hours, after which it was extracted with hexane (3×75 ml) that was discarded. The aqueous phase was made basic (pH 13) with 35% aqueous sodium hydroxide, then extracted with dichloromethane (3×120 ml), the combined extracts were washed with brine (2×80 ml), dried (MgSO$_4$) and the solvent evaporated to give an oil (9.2 g) which was purified by chromatography on a silica gel column. Elution with methanol/dichloromethane/ammonia 4/96/1 gave the ketone (7.0 g, 37.9% yield for the two steps). $^1$H-NMR CDCl$_3$) δ 1.40 (d, J=7.0 Hz, CH$_3$C), 1.75-2.15 (m, 4H), 2.20-2.80 (m, 4H), 2.32 (s, CH$_3$N), 2.57 and 2.65 (2d, J=17.2 Hz, CH$_2$C=O), 3.59 (q, J=7.0 Hz, CHS).

(b) Synthesis of 2,8-dimethyl-1-thia-8-aza-spiro[4.5]decan-3-one oxime. A solution of 2,8-dimethyl-1-thia-8-aza-spiro[4.5]decane-3-one (0.669 g, 3.36 mmol) in methanol (9 ml) was added to a solution of hydroxylamine hydrochloride (0.270 g, 3.88 mmol) and sodium acetate (0.320 g, 3.90 mmol) in water (1.5 ml). The mixture was heated at 80° C. for 2 hours. The solvents were removed at reduced pressure and the residue chromatographed on a silica gel column. Elution with methanol/dichloromethane/ammonia [5/94/1] gave first the anti-configuration oxime (0.267 g) and then a mixture of the two isomers (syn- and anti-) of the oxime (0.316 g) (81% yield). The anti-isomer was crystallized from ethyl acetate. mp. 148-149° C. $^1$H-NMR (CDCl$_3$, anti isomer) δ 1.46 (d, J=6.6, CH$_3$C), 1.73-1.96 (m, 3H), 2.05 (m, 1H), 2.15-2.40 (m, 1H), 2.32 (s, CH$_3$N), 2.47 (m, 1H), 2.70 (m, 2H), 2.78 and 2.86 (2d, J=17.4 Hz, CH$_2$C=N), 3.99 (q, J=6.6 Hz, CHS), 10.1 (bs, —NOH). $^{13}$C-NMR (CDCl$_3$, anti isomer) δ 19.7 (CH$_3$), 38.2 (CH$_2$), 38.9 (CH$_2$), 42.5 (CH), 42.8 (bs, CH$_2$), 45.9 (CH$_3$), 52.3 (C), 53.1 (CH$_2$), 53.4 (CH$_2$), 163.7 (C). Gc-Ms m/z 215 (M+1)$^+$, 197 (M–OH)$^+$, 96. $^1$H-NMR (CDCl$_3$, syn isomer, calculated by subtracting the NMR spectrum for the anti isomer from the NMR spectrum for the mixture of syn and anti isomers) δ 1.48 (d, J=6.8, CH$_3$C), 1.60-1.73 (m, 1H), 1.74-1.95 (m, 2H), 1.95-2.25 (m, 2H), 2.31 (s, CH$_3$N), 2.44 (m, 1H), 2.54 and 2.77 (2d, J=14.5 Hz, CH$_2$C=N), 2.60-2.90 (m, 2H), 4.37 (q, J=6.7 Hz, CHS), 10.2 (bs, NOH). $^{13}$C-NMR (CDCl$_3$, syn isomer) δ 21.0 (CH$_3$), 37.9 (CH$_2$), 38.2 (CH$_2$), 38.4 (CH), 46.0 (CH$_3$), 46.6 (bs, CH$_2$), 51.7 (C), 52.6 (CH$_2$), 53.8 (CH$_2$), 163.8 (C).

(c) Synthesis of 2,8-dimethyl-1-thia-8-aza-spiro[4.5]dec-3-ylamine: To a stirred suspension of lithium aluminum hydride (1.00 g, 26.35 mmol) and aluminum chloride (0.110 g, 0.825 mmol) in dry tetrahydrofuran (45 ml) under nitrogen, at room temperature, a solution of 2,8-dimethyl-1-thia-8-aza-spiro[4.5]decan-3-one oxime (1.24 g, 5.79 mmol) was slowly added. Stirring at room temperature was continued for three days. The reaction mixture was then cooled (water-ice bath) and water (3.0 ml) was added slowly, then aqueous sodium hydroxide solution (15%, 4.0 ml) and then water (4.0 ml). The precipitate was filtered and washed with a small amount of dichloromethane. The combined filtrate and washings were evaporated to give oil that was purified by chromatography on a silica gel column eluted with 10% methanol-89% dichloromethane-1% ammonia to give the amine as an oil (0.430 g, 37% yield). $^1$H-NMR data indicates that the product consists of two pairs of diastereoisomers, one pair being more abundant then the other. In the following data, * denotes the more abundant isomers, # denotes the less abundant isomers. $^1$H-NMR (CDCl$_3$) δ 1.25$^\#$(d, J=6.9 Hz, CH$_3$C), 1.31* (d, J=6.4 Hz, CH$_3$C), 1.60-2.08 (m, 4H), 1.72 (m, one of CH$_2$CNH$_2$), 2.08-2.45 (m, 2H), 2.18 (dd, one of CH$_2$CNH$_2$), 2.29 (s, CH$_3$N), 2.67 (m, 2H), 3.00* (m, CHS), 3.10 (m, CHNH$_2$), 3.37$^\#$(m, CHS); GC-ms m/z 201 (M+1)$^+$, 184 (M−NH$_2$)$^+$.

(d) Synthesis of N-(2,8-dimethyl-1-thia-8-azaspiro[4.5]dec-3-yl)-3-(1H-indole-3-yl)-propionoamide (AF 731). To a stirred solution of 2,8-dimethyl-1-thia-8-aza-spiro[4.5]dec-3-ylamine (0.375 g, 1.872 mmol) in dichloromethane (20 ml) at room temperature a solution of 1,3-dicyclohexylcarbodiimide (0.520 g, 2.52 mmol) in dichloromethane (8 ml) then 3-indolepropionic acid (0.458 g, 2.42 mmol) in dichloromethane (15 ml) were added. The reaction mixture was stirred at room temperature for three days. The solid formed was filtered and washed with small amount of dichloromethane, the combined filtrate and washing were evaporated to give a foam which was purified by silica gel column chromatography. Elution with solvent mixtures of 5 to 7% methanol in dichloromethane containing 1% ammonia gave first the product as a mixture of isomers (325 mg, 46.7% yield) and then unreacted amine (90 mg). $^1$H-NMR data indicates that the product consists of two pairs of diastereoisomers, one pair being more abundant the other. In the following data, * denotes the more abundant isomers, # denotes the less abundant isomers. $^1$H-NMR (CDCl$_3$) δ 0.99$^\#$ (d, J=6.9, CH$_3$C), 1.19* (d, J=6.6, CH$_3$C), 1.53 and 2.05 (2m, CH$_2$CHNH), 1.60-2.18 (m, 4H), 2.18-2.85 (m, 2H), 2.28$^\#$(s, CH$_3$N), 2.30* (s, CH$_3$N), 2.59 (m, 2H), 2.95* (m, CHS), 3.13 (t, 2H), 3.50$^\#$(m, CHS), 4.24* (m, CHN), 4.51$^\#$(m, CHN), 5.28* (d, J=8.7 Hz, NHCO), 5.55$^\#$(d, J=8.4 Hz, NHCO), 7.03* (d, J=2.3 Hz, 1H Ar), 7.04$^\#$(d, J=2.4 Hz, 1H Ar), 7.11 (t, 1H Ar), 7.20 (m, 1H Ar), 7.38 (d, J=8.0 Hz, 1H Ar), 7.60 (d, J=7.8 Hz, 1H Ar), 8.22 (bs, NH indole).

Example 26

(3E)-2,8-dimethyl-1-oxa-8-azaspiro[4.5]decan-3-one-O-[3-(1H-indol-3-yl)propanoyl]oxime (AF733)

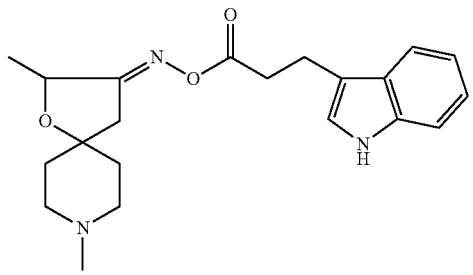 [SMILES: CC1OC2(CCN(C)CC2)C/C1=N\OC(=O)CCc1c[nH]c2ccccc12]

Carbonyldiimidazole (CDI) (0.19 g, 1.2 mmol) was added to a solution of 3-indole propionic acid (0.22 g, 1.2 mmol) in dry THF (10 ml) under an argon atmosphere. The reaction mixture was stirred for 0.5 h at room temperature, then dimethyl-1-oxa-8-azaspiro[4.5]decan-3-one oxime (0.23 g, 1.2 mmol, prepared according to the procedure of Tsukamoto et. al. *Chem. Pharma. Bull.* 1995, 43, 842-852) was added. The reaction mixture was stirred for 4 h at room temperature and then for 8 h at 45° C. The reaction mixture was cooled to room temperature, dichloromethane (80 ml) was added and the mixture was washed with water (10 ml). The two phases were separated and the aqueous phase was extracted with dichloromethane (30 ml). The organic phases were combined, dried with anhydrous sodium sulfate, filtered and the filtrate was concentrated under reduced pressure. The residue was purified by flash chromatography in a Combi-Flash Companion system (Isco, Inc) (HP 12-gold silica column, CH$_2$Cl$_2$/MeOH/NH$_4$OH 90/10/1) followed by further flash chromatography in a Combi-Flash Companion system (Isco, Inc) (HP 12-gold silica column, CH$_2$Cl$_2$/MeOH/NH$_4$OH 120/10/1). The residue was triturated in ether to give AF733 (104 mg), obtained as a white solid. $^1$H NMR (CDCl$_3$, 300 MHz) δ 8.17 (br s, 1H, NH-indole), 7.60 (d, J=7.73 Hz, 1H, CHC arom), 7.35 (d, J=7.98 Hz, 1H, CHC arom), 7.19 (app t, J=7.76 Hz, 1H, CHCH arom), 7.12 (app t, J=7.43 Hz, 1H, CHCH arom), 7.04 (d, J=2.11 Hz, 1H, CHNH arom), 5.56 (q, J=6.3 Hz, 1H, CHCH$_3$), 3.18 (t, J=7.37 Hz, 2H, CH$_2$), 2.83 (t, J=7.41 Hz, 2H, COCH$_2$), 2.40 (ABq, J=18.6 Hz, 2H, CH$_2$), 2.5-2.3 (m, 4H), 2.28 (s, 3H, NCH$_3$), 1.74 (2m, 3H), 1.5 (m, 1H), 1.43 (d, J=6.36 Hz, 3H, CH$_3$—CH) ppm; $^{13}$C NMR (CDCl$_3$, 300 MHz) δ 173.4 (C), 171.0 (C), 136.5 (C), 127.3 (C), 122.2 (CH), 122.1 (CH), 119.5 (CH), 118.8 (CH), 114.5 (C), 111.4 (CH), 78.7 (C), 72.5 (CH), 52.5 (CH$_2$), 52.2 (CH$_2$), 46.1 (CH$_3$), 40.0 (CH$_2$), 37.4 (CH$_2$), 34.4 (CH$_2$), 33.7 (CH$_2$), 20.9 (CH$_2$), 19.5 (CH$_3$) ppm.

Example 27

Synthesis of (D)-2-amino-1-(2,8-dimethyl-1-thia-3,8-diaza-spiro[4.5]dec-3-yl)-3-(1H-indol-3-yl)-propan-1-one (AF728)

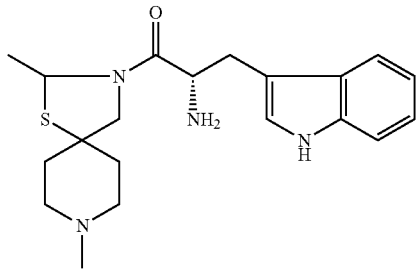 [SMILES: CC1SC2(CCN(C)CC2)CN1C(=O)[C@@H](N)Cc1c[nH]c2ccccc12]

1) To a stirred solution of 2,8-dimethyl-1-thia-3,8-diaza-spiro[4.5]decane (0.97 g, 5.2 mmol) in dichloromethane (100 ml) at room temperature was added dicyclohexylcarbodiimide (DCC) (1.44 g, 6.98 mmol) followed by addition of N-Boc-D-tryptophan (1.88 g, 6.2 mmol). The resulting solution was stirred at room temperature for 48 h. During the reaction a white solid precipitated. After filtration the solvent was evaporated and the crude product was purified by flash chromatography (silica, CH$_2$Cl$_2$/MeOH/NH$_4$OH 90/10/1) to give (R)-3-(2,8-dimethyl-1-thia-3,8-diaza-spiro[4.5]dec-3-yl)-2-(1H-indol-3-ylmethyl)-3-oxo-propionic acid tert-butyl ester (1.1 g) as a solid.

2) To a stirred solution of (R)-3-(2,8-dimethyl-1-thia-3,8-diaza-spiro[4.5]dec-3-yl)-2-(1H-indol-3-ylmethyl)-3-oxo-propionic acid tert-butyl ester (0.9 g, 2.1 mmol) in dichloromethane (20 ml) at room temperature was added trifluoroacetic acid (TFA, 1.2 ml, 16.2 mmol). The resulting solution was stirred at room temperature until complete removal of the Boc protecting group. The reaction mixture was diluted with dichloromethane (20 ml), treated with Amberlyst A-21 resin (20 g; described in Srinivasan et al., Mol. Diversity. 9 (2005) 4, 291-293) for 1 h, filtered and washed with dichloromethane (20 ml). The combined filtrates were evaporated and the crude product was purified by flash chromatography (silica, $CH_2Cl_2$/MeOH/$NH_4OH$ 90/10/1) to give the title product (0.1 g) as a solid. $^1H$ NMR ($CDCl_3$, 300 MHz) δ 8.14 (br s, 1H, NH-indole), 7.62 (d, J=7.65 Hz, 1H, CHC arom), 7.38 and 7.37 (2d, J=7.96 Hz and J=7.88 Hz, 1H, CHC arom), 7.22 (app t, J=7.0 Hz, 1H, CHCH arom), 7.10 (app dt, J=1.0, 7.4 Hz, 1H, CHCH arom), 7.09 and 7.06 (two d, J=2.28 Hz and J=2.25 Hz 1H, CHNH arom), 5.48, 4.98 (2q, J=6.2 and J=6.3 Hz, 1H, $CHCH_3$), 4.42, 3.69 (2d, J=12.0 and J=11.6 Hz, 1H, CHHNCO), 3.98 and 3.92 (2t, J=7.3 and J=7.05 Hz, 1H, $CHCH_2$), 3.12 (m, 21-1, $CHCH_2$), 2.80 (d, J=11.4 Hz, 0.72H, CRUNCO), 2.6 (m, 2H), 2.3-2.2 (m, 1H), 2.26 and 2.25 (2s, 3H, $NCH_3$), 2.15-2.0 (m, 1H), 1.52, 1.38 (2d, J=6.3 and J=6.2 Hz, 3H, $CH_3$—CH) ppm.

Biological Assays

Compounds of formula I were tested for biological activity using a variety of assays.

The assay of intracellular calcium ion ($Ca^{2+}$) mobilization in cell cultures that have been stably transfected with a GPCR (e.g. mAChR subtypes) can provide information both on the activity (agonistic or antagonistic) of the tested compound, as well as on its selectivity for a particular receptor subtype. Levels of free intracellular $Ca^{2+}$ were determined in living cells by monitoring the fluorescence of the fluorescent $Ca^{2+}$ indicator, Fluo-4 NW (Molecular Probes, catalogue #36206). This method is useful for characterizing GPCR pharmacology and function. $Ca^{2+}$ measurement was performed using a NOVOstar® plate reader with an injector and a pipettor system (BMG Labtechnologies, Offenburg, Germany). One day before experiment, cells stably transfected with one of the muscarinic receptor subtypes M1-M5 were harvested and rinsed with culture medium (Dulbecco's Modified eagle medium, Gibco, UK) supplemented with 10% fetal bovine serum, MEME No-essential Amino Acids (GIBCO, UK), Glutamine, penicillin, streptomycin, amphotericin and G418 (Biological Industries, Israel) and evenly plated into black-wall clear optical bottom 96-well plate (Nunc, Rochester N.Y., USA) at a density of 40,000 cell/well. On the day of experiment, cells were fully confluent. Growth medium was removed and 80 µl of loading buffer, containing 2.5 mM probenecid (4-dipropylsulfamoyl)benzoic acid), was carefully added (loading buffer prepared according FLUO-4 NW calcium assay kit manual). Cell plates were incubated at 37° C. for 30 minutes, then at room temperature for an additional 30 minutes. To evaluate the effects of the tested compounds on intracellular $Ca^{2+}$ ($Ca^{2+}$-i), in some of the experiments EGTA [ethylene glycol tetraacetic acid] was used to eliminate the extracellular calcium source. EGTA (10 µl of 50 mM dissolved in HBSS (Hank's Buffered Salt Solution) was added to each well automatically using the NOVOstar injector system, followed shaking for 0.5 minute (1 mm width, 600 rpm) and then incubated for another 10 minutes. HBSS alone or test compounds dissolved in HMS were then added (10 µl) sequentially into separate wells using the NOVOstar robotic pipettor system. Fluorescence intensity was measured at 0.5 second intervals, for 25 seconds for each well, using an excitation wavelength of 485 nm (bandwidth 10 nm) and emission of 520 nm (bandwidth 10 nm), cutoff 515 nm.

To evaluate selectivity for a subtype of mAChR, in particular the M1 mAChR vs. M3 and M5 mAChR, the assays were calibrated using ligands that have a combined activity, e.g. M1 agonistic and M3 antagonistic or M1 agonistic and M5 antagonistic profiles, respectively. This can eliminate effects due to different receptor reserves in cell-based assays.

The compounds AF710, AF710B, AF711, AF711A, AF718C, AF721, AF730, AF730 AF730 II and AF733 were observed to be partial agonists on the M1 mAChR, and their relative agonistic activity at 100 µM vs. carbachol (full muscarinic agonist, 100%) follows the order AF733 (90%) >AF730 I (745)>AF710B (66%)>AF711A (45%)>AF718C (43%)>AF710 (40%)≥AF730 (40%)>AF730 II (36%) >AF711 (19%)>AF721 (13%) (see Table). The agonistic effects of these agonists were blocked by the M1 selective antagonist, pirenzepine. AF710B was found to be highly selective for the M1 mAChR and did not show detectable agonistic activity on the M2-M5 mAChR subtypes, respectively.

The compounds AF706, AF712-AF716, AF726 and AF727 (100 µM) showed antagonistic activity on the M1 mAChR as evidenced by a shift to the right of the concentration curve of carbachol (Table).

Figure 1B:
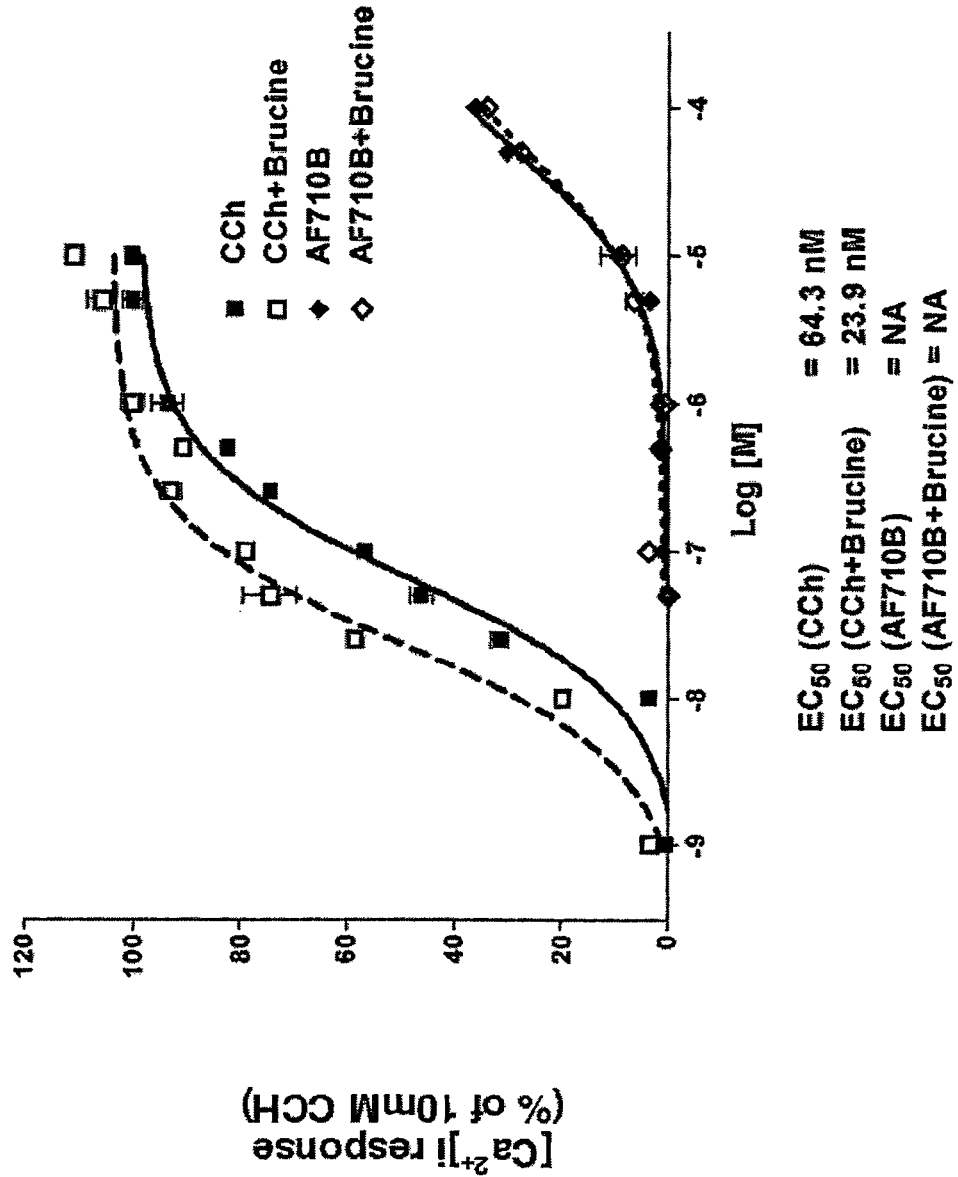

Orthosteric or allosteric M1 muscarinic agonist activity can be tested in the presence or absence of the allosteric M1 modulator brucine (Sur et al., Proc. Nat'l Acad. Sci. USA 2003, 100:13674-13679). Pre-incubation with Brucine (100 µM) of cell cultures stably transfected with the M1 mAChR or in Chinese hamster ovary cells stably transfected with both M1 mAChR and the human amyloid precursor protein 695 had caused a strong potentiating effect on the elevation of intracellular calcium ions-induced by orthosteric agonist such as carbachol, as shown by a leftward shift of their concentration-response curves, respectively. Brucine had no such effect on either AF710 or AF710B, and induced a slight inhibition of the effects of AF710B; taken together, these results show that AF710 and AF710B do not interact with the orthosteric site of the M1 mAChR, and thus are allosteric agonists. See FIG. 1.

The 3-(4,5-dimethylthiazol-2-yl)-2,5-diphenyl-tetrazolium bromide (MTT) assay measures changes that occur within the cells, involving mitochondria activation, indicative of a process that eventually leads to cell death (Fagarasan et al., Mol. Psychiat. 1996, 1:398-403). This assay is a specific, early indicator of the mechanism of β-amyloid-mediated cell death (Shearman et al., PNAS USA 1994, 91:1470-74). This assay was used to evaluate compounds of formulae I and II. Rat pheochromocytoma (PC12) cells cells were plated in 96 well plate at a density of 10,000 cells/well, and maintained in Dulbecco's modified Eagle medium (Gibco, Cat. 21969) supplemented with 5% fetal bovine serum (Biological Industries, Cat. 04-121-1A), 10% heat-inactivated horse serum (Gibco Cat. 26050), L-Glutamine 200 mM (Biological Industries, Cat.03-020-1C), Penicillin 10000 U/ml (Biological Industries, Cat 03-031-1C), and Amphotericin B 50 mg/ml (Biological Industries, Cat. 01-029-1C). The next day the medium was refreshed with serum free media and cells were treated with 5 µM β-amyloid 25-35 (H-1192.0001, Bachem) in the presence or absence of the test compound. Compounds were tested for 6 hours, respectively, at final concentrations ranging between 0.1 nM to 100 µM. 3-Indole-propionic acid (3-IPA, Cat. 220027, Sigma Aldrich) served as a reference antioxidant. 3-IPA, AF710 and AF711 protected cells against toxicity induced by Aβ25-35 (a peptide that has the sequence of amino acids (AA) 25-35 from beta-amyloid which has 40 or 42 amino acids) at a range of concentrations (10 µM-1 nM). These results show that AF710 and AF711 have antioxidant properties.

α-APPs Secretion studies following incubation with the tested compounds were performed as described in Haring, et al. J. Neurochem, 1998, 71:2094-103. Chinese Hamster Ovary (CHO) cells double transfected with human APP695 and with human M1 mAChR, or rat pheochromocytoma cells (PC12) stably transfected with rat M1 mAChR were seeded in 6-well plates at a density of $2 \times 10^6$ cells/well. A day later, cells were washed twice with serum free media, and treated with the test compound at various concentrations ranging from 0.1 nM to 100 μM. In each plate, one well served as a control (no treatment) and one well as a positive reference in which the cells were treated with either 1 or 100 μM carbachol (CCh) (maximal response). After 1 hour the conditioned medium was collected to cold Eppendorf tubes, which included a protease inhibitor cocktail (0.1 mM phenylmethylsulphonyl fluoride (PMSF); 5 μg/ml leupeptin; 5 μg/ml pepstatin and 5 units/ml aprotinin) for determining aAPPs release. The protein content of each sample was concentrated using Centricon tubes (Amicon, Beverly, Mass.). Following protein determination (Bio-Rad protein assay), equal protein amounts (30 μg protein/lane) were loaded on 4-12% NuPage Novex Bis-Tris Gels (Invitrogen, CA) and then subjected to electrophoresis. When electrophoresis was completed, gels were blotted onto Immuno-Blot PVDF membranes (0.2 μm, Bio-Rad Lab, CA) using Hoefer semi-dry transfer units (Semi-Phor, Hoefer Scientific Inst. San Francisco, Calif.). Membranes were then blocked with 5% fat powder milk dissolved in Dulbecco's phosphate buffer saline without calcium and magnesium (DPBS; Gibco, Cat 14200) with 0.1% Tween-20 (Sigma, Cat P5927). CHO cells double transfected with human APP695 and M1 mAChR APPs bands were probed using anti-amyloid beta protein (1:1000, monoclonal 6E10 antibody, MAB1560, Chemicon) and peroxidase-linked rabbit anti mouse IgG (1:5,000; Jackson Immuno Research, PA). PC12 cells stably transfected with M1 mAChR APPs bands were probed using the anti-Alzheimer precursor protein A4 (1:4,000; monoclonal 22C11 antibody, Boehringer Mannheim) and the peroxidase-linked rabbit anti mouse IgG (1:20,000; Jackson Immuno Research, PA). Following extensive washout, the membranes were treated with Western Lightning Chemiluminescence Reagent Plus (PerkinElmer Life Sciences, MA) followed by exposure to SuperRX film (Fuji Medical X-ray film, Tokyo, Japan). Quantitative determination of the total APPs bands was performed by Scion Image program (NaI, Bethesda, USA). Samples of control and CCh were assayed in parallel and thus enabled compilation of data from separate experiments.

AF710 enhanced the release of aAPPs in the transfected CHO and PC12 cells, through concentrations ranging from 0.1 nM to 1 μM. The elevated levels of aAPPs observed in the transfected PC12 cellswere not observed in PC12 cells which had not been transfected.

In comparison to the untreated control cells, the maximal aAPPs secretion in the doubly-transfected CHO cells was enhanced in the following order: AF710B (0.01 μM 225%) >AF710 (0.1 μM 175%)>AF710A (1 μM 125%).

Detection of GSK-3β levels was evaluated using western blotting in rat pheochromcytoma cells (PC12) stably transfected with M1 mAChR cell cultures treated with the tested compounds (+/−Aβ 25-35, 20 μM) using a protocol similar to that described in Fang et al., Mol. Cell. Biol. 2002, 22:2099-110), but using antibodies selective for Phospho-GSK3β (Ser 9), i.e. the inactive form of GSK3β (see Doble et al., J. Cell. Sci. 2003, 116:1175-86), purchased from Cell Signaling Technology, USA. This antibody does not detect the non-phosphorylated GSK-3β (up to 1 μg) and does not cross react with GSK-3α. Anti-GSK-3 (Santa Cruz Biotechnology) is a phosphorylation-independent monoclonal antibody reactive with both GSK-3α and GSK3β. In the same experiments the status of tau protein phosphorylation was studied using mouse anti Tau-1 monoclonal antibody (Chemicon, CAT number MAB3420), which recognizes an unphosphorylated epitope of tau. The presence of Aβ25-35 (20 μM) resulted in a 40-50% decreasein staining by Phospho-GSK3β (Ser 9), which labels the inactive form of GSK3β. This indicates an elevation in the presence of the active form. Aβ710B (100 μM-10 nM) inhibited the overactivation of GSK-3β induced by Aβ25-35 (20 μM). In the same experiments Aβ25-35 (20 μM) decreased by 40-60% the staining of Tau-1 and AF710B (100 μM-10 nM) restored these effects to control level. Taken together these results show that AF710B decreased overactivation of GSK3β and overphosphorylation of tau proteins.

Binding studies were performed using rat brain homogenates (cortex rich in M1 mAChR), as described in Fisher et al., J. Pharmacol. Exptl. Therap. 1991, 257:392-403. Cerebral cortex was dissected out and placed on ice, cleaned, weighed and transferred to 20 mM Tris-HCl buffer, 2 mM EDTA, pH 7.4. The tissue was homogenized in the buffer (1:10 weight/volume) using polytron homogenizer and after a −70° C. freeze/thaw cycle, the homogenates were centrifuged at 35,000 g at 4° C. for 10 min. The supernatant was removed and the pellets were resuspended in Tris buffer at a ratio of 1:6 (weight/volume). The homogenates were divided into aliquots of 1 ml each and then stored at −70° C. until use. The binding profile for the binding of test compound to mAChR was studied using the $M_1$ selective antagonist, [$^3$H]-pirenzepine ([$^3$H]PZ; specific activity 86 Ci/mmol, purchased from Perkin-Elmer, Mass., USA) in rat cortical membranes. Various concentrations of a tested compound (e.g. $10^{-9}$-$10^{-4}$ M final concentrations) were pipetted into $13 \times 100$ mm glass tubes containing [$^3$H]PZ (at final concentrations varying between 4-6 nM in each individual experiment), 20 mM Tris/Mn buffer, pH 7.4, containing 1 mM EDTA and 2 mM $MnCl_2$ and cortical membranes (diluted as specified above) altogether in a final volume of 0.2 ml. The total and non-specific binding were determined in the absence of competitive ligand or in the presence of 10 μM atropine, respectively. All assays were carried out in triplicate at 25° C. for 1 hour. At the end of the incubation period, the tubes were immersed in an ice bath and their contents were filtered. The bound material was trapped on pre-soaked (0.5% polyethylenimine for 1 hour) GF/B filters $317 \times 57$ mm (Whatman, Tamar, Jerusalem, Israel) using a Brandel system (M-24R, Gaithersburg, Md., USA). The filters were then dried and punched into vials. Scintillation fluid (Biodegradable counting scintillant, Amersham, Ill., USA) was added and the radioactivity was measured using a PerkinElmer TriCarb 2800 liquid scintillation counter. Competition curves, $K_H$, $K_L$, values were derived using the GraphPad Prism software program, version 3.0. In this study AF710B displayed a two-site binding curve toward M1 mAChR in rat cortical membranes, with a 5-fold order of magnitude interval between the two binding sites, a higher affinity binding site $K_H$=0.23 nM (37%) and a lower affinity binding site $K_L$=34.5 μM (63%).

A high-throughput profiling that consists of a broad collection of 80 transmembrane and soluble receptors, ion channels and monoamine transporters was performed on AF710B. It was specifically designed to provide information not only on potential limitations of drug candidates, but also for off-target activity identification. The results obtained indicate that AF710B binds to the following the M1 and M2 mAChR and to other receptors. In a further extension of this study, functional studies were done on most of these receptors. It was found that M1 mAChR-mediated effects of AF710B on downstream neurochemical readouts (e.g. aAPPs, GSK3β, tau) were detected at concentrations lower by 3-5 orders of magnitude vs. interactions with the other GPCR.

Acute toxicity study in rats: AF710B (1, 10 and 50 mg/kg) and an inactive vehicle for control were administered orally by gavage to groups of 3 male +3 female rats/dose and evaluated for possible toxic or other overt effects. On the day of dosing, careful clinical examinations were carried out and recorded periodically during the first 4 hours post-dosing and at the end of the respective working day. Thereafter, animals were inspected and clinical signs were recorded at least once daily throughout the entire 14-day observation period. Observations included changes in skin, fur, eyes, mucous membranes, occurrence of secretions and excretions (e.g. diarrhea) and autonomic activity (e.g. lacrimation, salivation, piloerection, pupil size, unusual respiratory pattern). Changes in gait, posture and response to handling, as well as the presence of bizarre behavior, tremors, convulsion, sleep and coma were also examined. No mortality occurred in any of the Test Item or Test Item Vehicle Control-treated animals prior to the scheduled euthanasia, carried out 14 days following the acute oral (PO) gavage administration. No obvious treatment-related adverse reactions were observed among any Test Item or Test Item Vehicle Control-treated animals on the respective day of dosing or during the entire 14-day observation period, excluding a slight decrease in motor activity and slight dyspnea, noted 5 minutes post dosing in a single male rat, subjected to the Test Item with dose level of 50 mg/kg and fully recovered 100 minutes post-administration. In view of the sequential method applied in the current study and in order to standardize, as much as possible, all body weight and body weight gain values, the respective percentage change in body weight vs. the day of dosing was calculated for each animal and group. No statistically significant differences were revealed among all Test Item-treated groups vs. the Vehicle Control group, excluding a statistically significant decrease ($p<0.05$) in the mean group percentage body weight change of one group of female rats (dose level of 10 mg/kg), noted 7 days post-dosing. All animals were subjected to a full detailed necropsy and gross pathological examination following the scheduled termination. At necropsy, all animals were subjected to thorough examination, including the external surface of the body, all orifices, cranial, thoracic and abdominal cavities and their contents. No gross pathological findings were evident macrosopically among all Test Item or Test Item Vehicle Control-treated animals at the time of their scheduled necropsy, carried out 14 days following the acute oral (PO) gavage administration. A Maximum Tolerated Dose (MTD) of the Test Item AF710B, following an acute oral (PO) gavage administration to the rat, was calculated.

Trihexyphenidyl is a selective M1 muscarinic antagonist that crosses the blood brain barrier and induces memory and learning impairments (Bymaster et al., J Pharmacol Exp. Ther. 267: 16-24, 1993; Roldan et al., Neurosci. Lett. 230: 93-96, 1997; Kimura et al., Brain Res. 834: 6-12, 1999). Therefore, systemic administration of this compound is useful as a pharmacological tool to investigate the role of brain $M_1$ muscarinic receptors in learning and memory processes. Naive Wistar rats were used in the experiments below. The passive avoidance (PA) task consists of a training (acquisition) phase and a retention phase. In the training procedure each rat was individually placed in the small illuminated compartment and after 60 s. of familiarization/adaptation, the door to the large compartment was opened and the latency to enter was measured (Initial Latency). Immediately following entry into the dark compartment, the door was closed and inescapable foot shock (0.6 mA for 3 s) was delivered through the grid floor. A cutoff point of 180 s was used for initial latency. Animals that failed to enter (step-through) within 180 s were excluded from the experiment. After the acquisition trial the rat was returned to its home cage. Retention of the passive avoidance task was measured 24 h later, by again placing the rat in the light compartment and after a 60 s adaptation interval, the door was opened and the latency to re-enter the dark compartment was measured. A cutoff point of 300 s was used for retention latency. Animals that failed to step through within 300 s were removed from the apparatus and a 300 s latency was recorded for them. Rats were divided into 2 groups. One group (N=40) was treated with trihexyphenidyl (5 mg/kg, s.c) and the second group (N=30) was treated with double distilled water (DDW 1 ml/kg, s.c.), 30 min before the shock. In each group, rats were divided into 4 treatment subgroups (N=9-11 for the triheyphenidyl-treated group and N=7-8 for the DDW-treated group): one subgroup was treated with DDW (10 ml/kg, p.o.), and three subgroups were treated with AF710B (0.01, 0.03 & 0.1 mg/kg, p.o.) 60 min before the shock. A significant interaction was found between trihexyphenidyl and treatments ($F(2/63)=4.0$, $p<0.023$). Retention latency of trihexyphenidyl rats treated with DDW (54.22±14.60 s) was significantly shorter than that of control rats treated with DDW (242.00±30.60 s) ($p<0.001$). However, the retention latency of trihexyphenidyl rats treated with AF710B 0.01 mg/kg (252.50±32.30 s), and 0.03 mg/kg (178.82±32.70 s) was significantly longer than that of trihexyphenidyl rats treated with DDW ($p<0.01$–$0.001$). The retention latency of trihexyphenidyl rats treated with AF710B 0.1 mg/kg (122.00±34.60 s) was not different from that of trihexyphenidyl rats treated with DDW. Thus AF710B was found effective even at doses of 0.01 mg/kg, po (0.028 μmole/kg, po).

In order to assess whether compounds of formula I would be likely be transported to the CNS, partition coefficients for the compounds shown in Table 1 were calculated. Partition coefficients are a measurement of lipophilicity and can be expressed numerically as 'log P' values, where log P is the log of the octanol-water or buffer partition coefficient. Log P values can either be determined experimentally, including by HPLC methods, or by predictive computational methods. The higher the value of log P, the greater the lipophilicity and thus the lipid solubility of the chemical entity in question. Substances with high log P values dissolve better in fats and oils than in water. This enhances their ability to enter lipid (fat-based) membranes in the body by passive diffusion, thereby enhancing their potential for absorption. Many drugs have a log P value of between 1 and 4, making them suitable for oral methods of delivery. Thus the logP value provides a general guideline as to whether a drug may gain rapid access to the CNS or not. The log P for the compounds shown in Table 1, calculated using the web-based program available through "Molinspiration" (www.molinspiration.com/cgi-bin/properties, Molinspiration Calculation Services), a package for calculation of molecular properties, was in all cases between 1 and 4.

TABLE 1

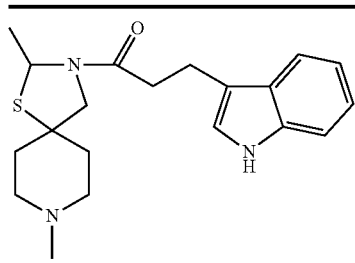

AF710 and its enatiomers AF710A & AF710B

M.W. = 357.5  
LogP = 3.36 *  
Effects on M1 mAChR #:  
M1 agonist at 100 μM vs. carbachol (full muscarinic agonist, 100%):  
AF710 (40%)  
AF710B (66%)  
AF710A (antagonist, K$_d$ = 31 μM)

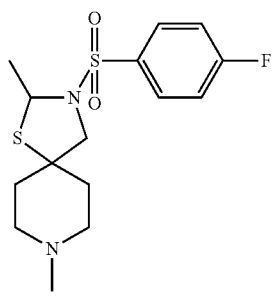

AF716

M.W. = 344.5  
LogP* = 2.64  
Effects on M1 mAChR #:  
AF716 (M1 antagonist, K$_d$ = 7.7 μM)

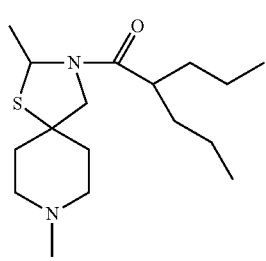

AF717

M.W. = 312.5  
LogP = 4.14 *  
Effects on M1 mAChR #  
Antagonist at 100 μM on M1 mAChR inhibiting carbachol-induced effects from 100% to <25%

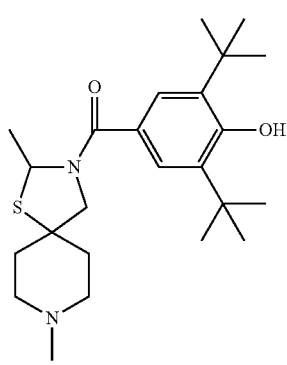

AF723

M.W. = 418.6  
LogP = 5.18 *  
Effects on M1 mAChR #  
Antagonist at 100 μM on M1 mAChR inhibiting carbachol-induced effects from 100% to <50%

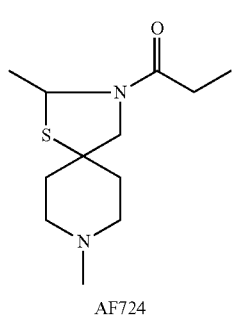

AF724

M.W. = 242.4  
LogP = 1.77 *  
Effects on M1 mAChR #  
Antagonist at 100 μM on M1 mAChR inhibiting carbachol-induced effects from 100% to <50%

TABLE 1-continued

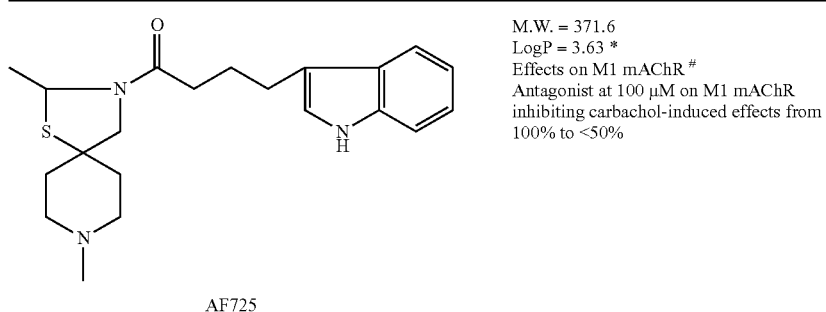

AF725

M.W. = 371.6
LogP = 3.63 *
Effects on M1 mAChR [#]
Antagonist at 100 µM on M1 mAChR
inhibiting carbachol-induced effects from
100% to <50%

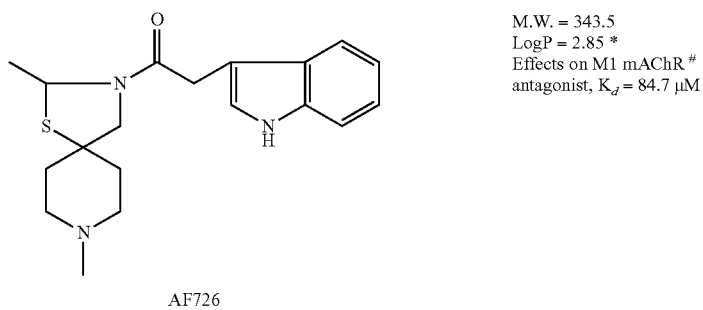

AF726

M.W. = 343.5
LogP = 2.85 *
Effects on M1 mAChR [#]
antagonist, $K_d$ = 84.7 µM

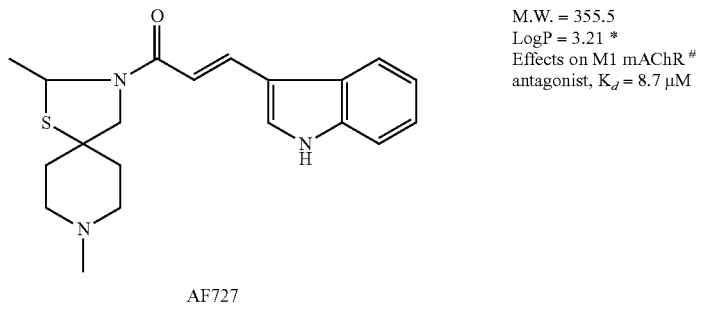

AF727

M.W. = 355.5
LogP = 3.21 *
Effects on M1 mAChR [#]
antagonist, $K_d$ = 8.7 µM

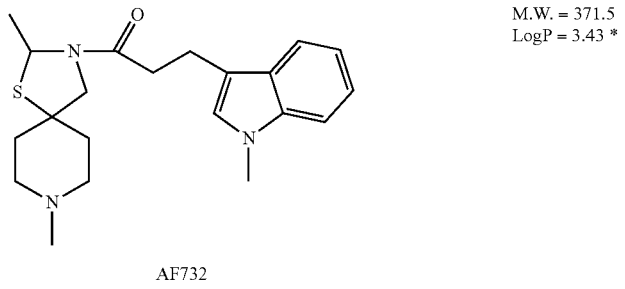

AF732

M.W. = 371.5
LogP = 3.43 *

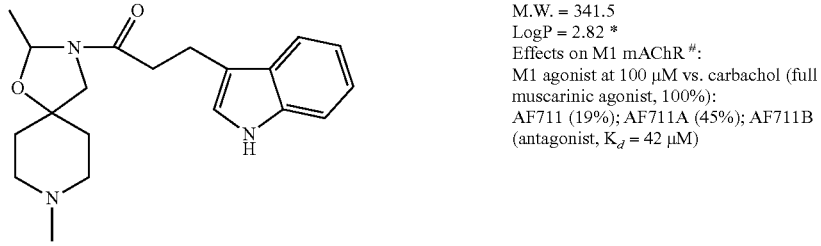

AF711 (AF711A & AF711B)

M.W. = 341.5
LogP = 2.82 *
Effects on M1 mAChR [#]:
M1 agonist at 100 µM vs. carbachol (full
muscarinic agonist, 100%):
AF711 (19%); AF711A (45%); AF711B
(antagonist, $K_d$ = 42 µM)

TABLE 1-continued
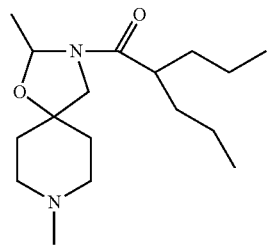
AF712
M.W. = 296.5
LogP = 3.60 *
Effects on M1 mAChR [#]
antagonist, $K_d$ = 22.6 μM
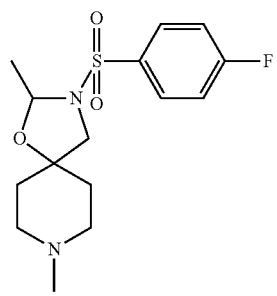
AF715
M.W. = 328.5
LogP = 2.10 *
Effects on M1 mAChR [#]
antagonist, $K_d$ = 2.5 μM
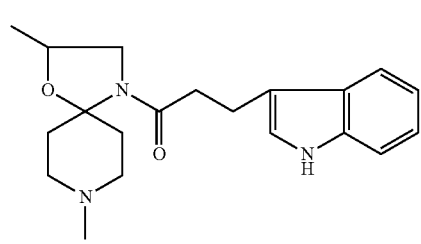 [SMILES: CC1CN(C(=O)CCc2c[nH]c3ccccc23)C2(CCN(C)CC2)O1]
AF706
M.W. = 341.5
LogP = 2.82 *
Effects on M1 mAChR [#]
antagonist, $K_d$ = 39.7 μM
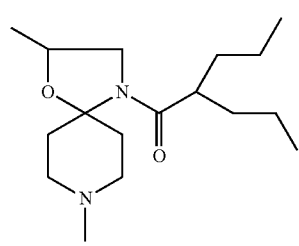 [SMILES: CCCC(CCC)C(=O)N1CC(C)OC12CCN(C)CC2]
AF713
M.W. = 296.5
LogP = 3.60 *
Effects on M1 mAChR [#]
antagonist, $K_d$ = 112.7 μM
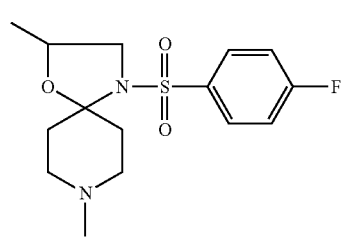
AF714
M.W. = 328.4
LogP = 2.1 *
Effects on M1 mAChR [#]
antagonist, $K_d$ = 9.7 μM TABLE 1-continued

| Structure | Properties |
|---|---|
| 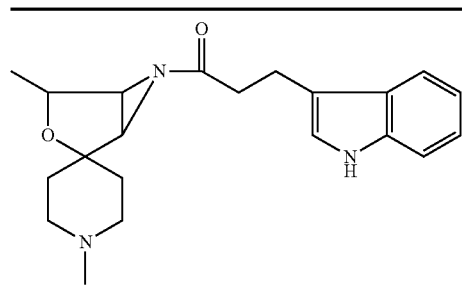<br>AF718C | M.W. = 353.5<br>LogP = 2.67 *<br>Effects on M1 mAChR #<br>M1 agonist at 100 μM vs. carbachol (full muscarinic agonist, 100%):<br>AF718C (43%) |
| 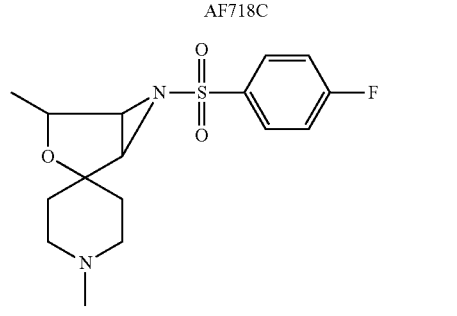<br>AF721 | M.W. = 340.4<br>LogP = 1.95 *<br>M1 agonist at 100 μM vs. carbachol (full muscarinic agonist, 100%):<br>AF721 (13%) |
| 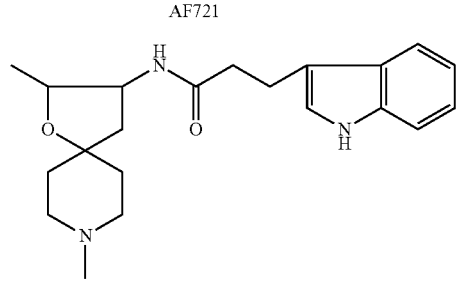<br>AF730, AF730 I,<br>AF730 II | M.W. = 355.5<br>LogP = 2.85 *<br>Effects on M1 mAChR #:<br>M1 agonist at 100 μM vs. carbachol (full muscarinic agonist, 100%):<br>AF730 (40%)<br>AF730 I (74%)<br>AF730 II (36%) |
| 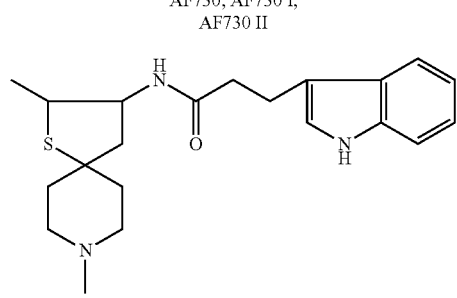<br>AF731 | M.W. = 371.5<br>LogP = 3.39 * |
| 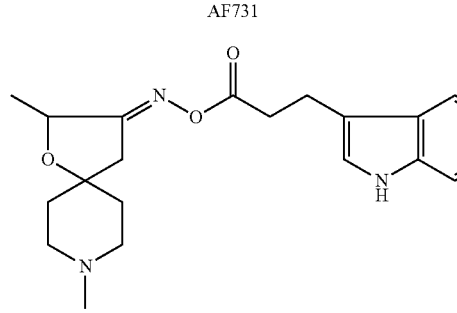<br>AF733 | M.W. = 369.5<br>LogP = 3.53 *<br>Effects on M1 mAChR #:<br>M1 agonist at 100 μM vs. carbachol (full muscarinic agonist, 100%):<br>AF733 (90%) |

* Calculated using the web-based program available through "*Molinspiration*", a package for calculation of molecular properties (Molinspiration Calculation Services, www.molinspiration.com/cgi-bin/properties).
Effects on M1 mAChR were evaluated via mobilization of intracellular Ca ions, as described above. The M1 mAChR represents a particular GPCR.

The present invention is not limited to the compounds found in the above examples, and many other compounds falling within the scope of the invention may also be prepared using the procedures set forth in the above synthetic schemes.

The preparation of additional compounds of formula I using these methods will be apparent to one of ordinary skill in the chemical arts.

The invention has been described in detail with particular reference to some embodiments thereof, but it will be understood by those skilled in the art that variations and modifications can be effected within the spirit and scope of the invention.

The invention claimed is:

1. A spiro compound of formula I:

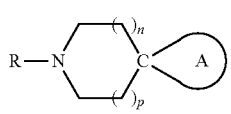

wherein A is selected from the group consisting of

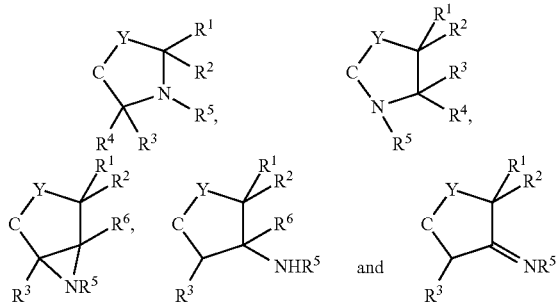

wherein in all structures the carbon indicated by "C" denotes the spiro carbon,

R is selected from the group consisting of H and optionally substituted $C_{1-6}$ alkyl, n and p are each independently selected from 0, 1 and 2, provided that n+p=2;

Y is —O— or —S—;

$R^1$, $R^2$, $R^3$, $R^4$, and $R^6$ are each independently selected at each occurrence from H, optionally substituted $C_{1-6}$ alkyl, optionally substituted $C_{1-6}$ alkoxy, optionally substituted $C_{1-6}$ hydroxyalkyl, optionally substituted $C_{2-6}$ alkenyl, and optionally substituted phenyl;

$R^5$ is selected from the group consisting of optionally substituted —C(O)—$(C_{1-3})$-indol-3-yl, —$SO_2$-4-fluorophenyl, —C(O)CH(n-propyl)$_2$, —C(O)-(4-hydroxy-3,5-di-tertbutylphenyl), —C(O)—CH(NH$_2$)—CH$_2$-indol-3-yl, and —C(O)—CH$_2$CH$_3$;

provided that when A is other than

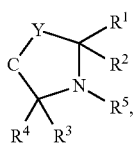

the compound is selected from the group consisting of:

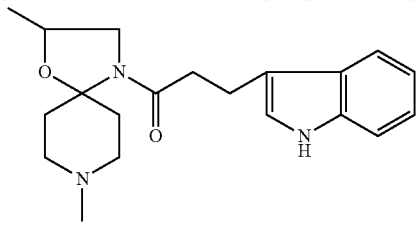

(1-(2,8-dimethyl-1-oxa-4,8-diazaspiro[4.5]dec-4-yl-3-(1H-indol-3-yl)-propan-1-one),

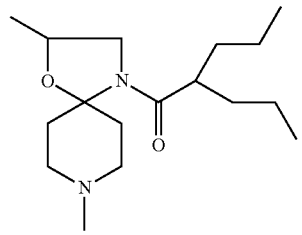

(1-(2-dimethyl-1-oxa-4,8-diaza-spiro[4.5]dec-4-yl)-2-propyl-pentan-1-one),

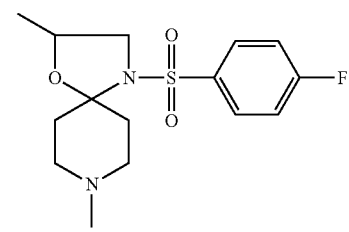 [SMILES: CC1CN(S(=O)(=O)c2ccc(F)cc2)C2(CCN(C)CC2)O1]

(4-(4-fluoro-benzenesulfonyl)-2,8-dimethyl-1-oxa-4,8-diaza-spiro[4.5]-decane),

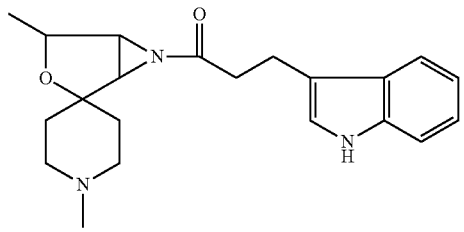 [SMILES: CC1OC2(CCN(C)CC2)C2C1N2C(=O)CCc1c[nH]c2ccccc12]

(1',4-dimethyl-6-(3-indolpropionyl)-spiro-(3-oxa-6-aza-bicyclo[3.1.0]-hexane-2,4'-piperidine)), and

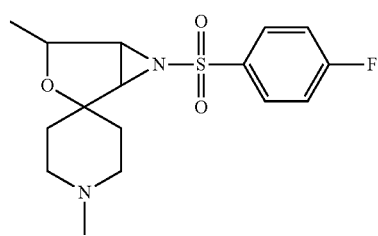 [SMILES: CC1OC2(CCN(C)CC2)C2C1N2S(=O)(=O)c1ccc(F)cc1]

(1',4-dimethyl-6-[3-(4-fluorobenzenesulfonyl)]-spiro-(3-oxa-6-aza-bicyclo[3.1.0]hexane-2,4'-piperidine)),

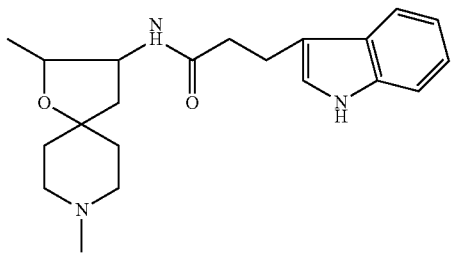 [SMILES: CC1OC2(CCN(C)CC2)CC1NC(=O)CCc1c[nH]c2ccccc12]

N-(2,8-dimethyl-1-oxa-8-aza-spiro[4.5]dec-3-yl)-3-(1H-indol-3-yl)-propionamide,

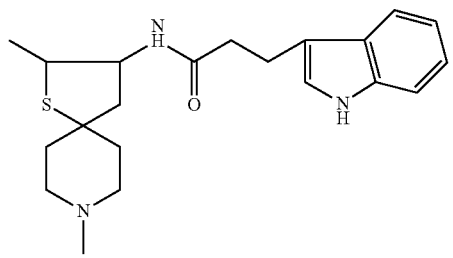 [SMILES: CC1SC2(CCN(C)CC2)CC1NC(=O)CCc1c[nH]c2ccccc12]

N-(2,8-Dimethyl-1-thia-8-aza-spiro[4.5]dec-3-yl)-3-(1H-indol-3-yl)-propionamide, and

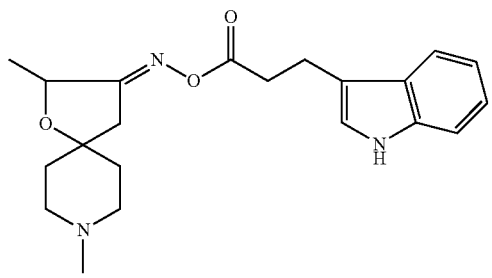 [SMILES: CC1OC2(CCN(C)CC2)C/C1=N\OC(=O)CCc1c[nH]c2ccccc12]

(3E)-2,8-dimethyl-1-oxa-8-azaspiro[4.5]decan-3-one-O-[3-(1H-indol-3-yl)propanyl]oxime;
or a pharmaceutically acceptable salt thereof.

2. A compound according to claim 1 wherein R is methyl.
3. A compound according to claim 1 wherein p and n are each 1.
4. A compound according to claim 1 wherein A is

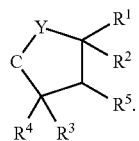

5. A compound according to claim 1 wherein $R^1$ is methyl.
6. A compound according to claim 5 wherein $R^2$ is H.
7. A compound according to claim 5 wherein $R^3$ and $R^4$ are each H.
8. A compound according to any claim 1 wherein Y is S.
9. A compound according to claim 1 wherein Y is O.

10. A compound according to claim 1 wherein $R^5$ is optionally substituted —C(O)—$(C_{1-3})$-indol-3-yl.
11. A compound according to claim 10 wherein $R^5$ is selected from the group consisting of —C(O)—$CH_2$-indol-3-yl, —C(O)—$CH_2CH_2$-indol-3-yl, —C(O)—$CH_2CH_2CH_2$-indol-3-yl, trans —C(O)—CH=CH-indol-3-yl and —C(O)—CH($NH_2$)—$CH_2$-indol-3-yl.
12. A compound according to claim 1 wherein A is

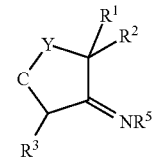

and $R^5$ is —O—C(=O)—$CH_2CH_2$-indol-3-yl.
13. A compound according to claim 1 wherein $R^5$ is selected from the group consisting of —$SO_2$-4-fluorophenyl, —C(O)CH(n-propyl)$_2$, $R^5$ is —C(O)-(4-hydroxy-3,5-di-tert-tbutylphenyl) and —C(O)—$CH_2CH_3$.
14. A compound according to claim 1 which is selected from one of the following:

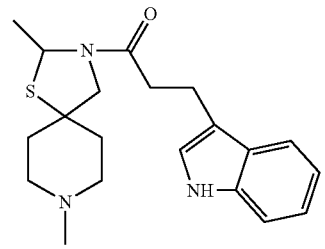 [SMILES: CC1SC2(CCN(C)CC2)CN1C(=O)CCc1c[nH]c2ccccc12]

(1-(2,8-dimethyl-1-thia-3,8-diazaspiro[4.5]dec-3-yl)-3-(1H-indol-3-yl)propan-1-one),

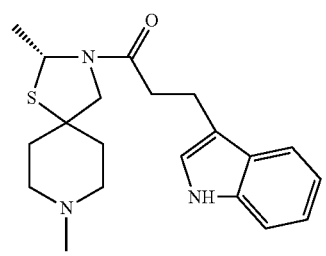 [SMILES: C[C@H]1SC2(CCN(C)CC2)CN1C(=O)CCc1c[nH]c2ccccc12]

((R)-1-(2,8-dimethyl-1-thia-3,8-diazaspiro[4.5]dec-3-yl)-3-(1H-indol-3-yl)propan-1-one),

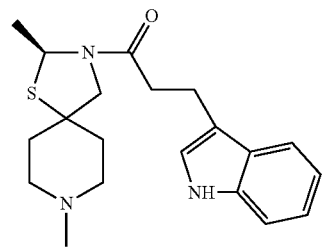 [SMILES: C[C@@H]1SC2(CCN(C)CC2)CN1C(=O)CCc1c[nH]c2ccccc12]

((S)-1-(2,8-dimethyl-1-thia-3,8-diazaspiro[4.5]dec-3-yl)-3-(1H-indol-3-yl) propan-1-one),

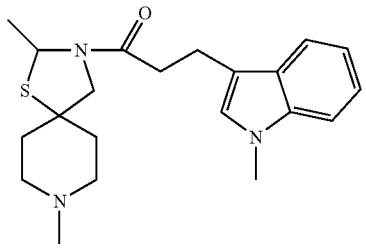 [SMILES: CC1SC2(CCN(C)CC2)CN1C(=O)CCc1cn(C)c2ccccc12]

1-(2,8-Dimethyl-1-thia-3,8-diazaspiro[4.5]dec-3-yl)-3-(1-methyl-indol-3-yl)propan-1-one,

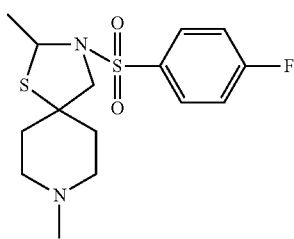 [SMILES: CC1SC2(CCN(C)CC2)CN1S(=O)(=O)c1ccc(F)cc1]

(3-(4-fluorobenzenesulfonyl)-2,8-dimethyl-1-thia-3,8-diazaspiro[4.5]-decane),

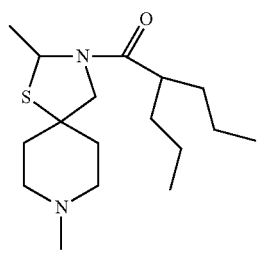 [SMILES: CCCC(CCC)C(=O)N1CC2(CCN(C)CC2)SC1C]

(1-(2,8-dimethyl-1-thia-3,8-diazaspiro[4.5]dec-3-yl)-2-propylpentan-1-one),

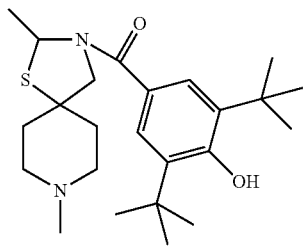 [SMILES: CC1SC2(CCN(C)CC2)CN1C(=O)c1cc(C(C)(C)C)c(O)c(C(C)(C)C)c1]

((3,5-di-tert-butyl-4-hydroxy-phenyl)-(2,8-dimethyl-1-thia-3,8-diaza-spiro[4.5]dec-3-yl)-methanone),

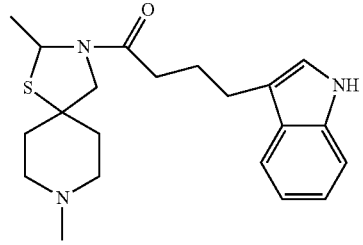 [SMILES: CC1SC2(CCN(C)CC2)CN1C(=O)CCCc1c[nH]c2ccccc12]

(1-(2,8-dimethyl-1-thia-3,8-diazaspiro[4.5]dec-3-yl)-4-(1H-indol-3-yl)butan-1-one),

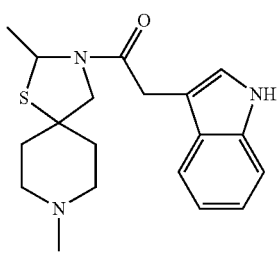 [SMILES: CC1SC2(CCN(C)CC2)CN1C(=O)Cc1c[nH]c2ccccc12]

(1-(2,8-dimethyl-1-thia-3,8-diazaspiro[4.5]dec-3-yl)-2-(1H-indol-3-yl)ethan-1-one),

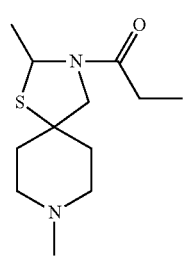 [SMILES: CCC(=O)N1CC2(CCN(C)CC2)SC1C]

(1-(2,8-dimethyl-1-thia-3,8-diazaspiro[4.5]dec-3-yl)-propan-1-one),

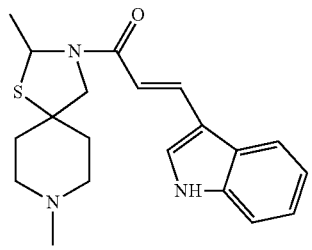

65

(1-(2,8-dimethyl-1-thia-3,8-diazaspiro[4.5]dec-3-yl)-3-(1H-indol-3-yl)prop-2-ene-1-one),

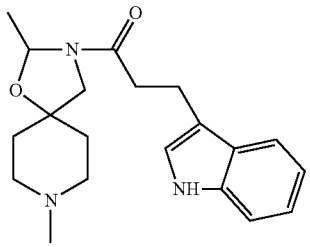

1-(2,8-dimethyl-1-oxa-3,8-diazaspiro[4.5]dec-3-yl)-3-(1H-indol-3-yl)-propan-1-one,

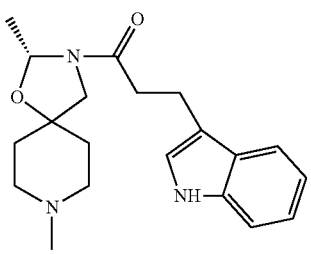

((R)-1-(2,8-dimethyl-1-oxa-3,8-diazaspiro[4.5]dec-3-yl)-3-(1H-indol-3-yl)-propan-1-one),

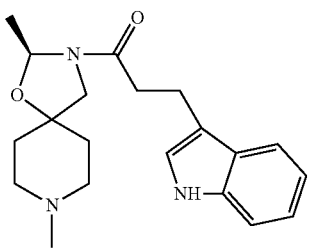 [SMILES: C[C@@H]1OC2(CCN(C)CC2)CN1C(=O)CCc1c[nH]c2ccccc12]

((S)-1-(2,8-dimethyl-1-oxa-3,8-diazaspiro[4.5]dec-3-yl)-3-(1H-indol-3-yl)-propan-1-one),

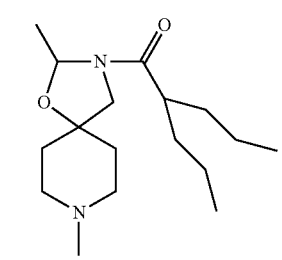 [SMILES: CCCC(CCC)C(=O)N1CC2(CCN(C)CC2)OC1C]

66

(1-(2,8-dimethyl-1-oxa-3,8-diaza-spiro[4.5]dec-3-yl)-2-propyl-pentan-1-one),

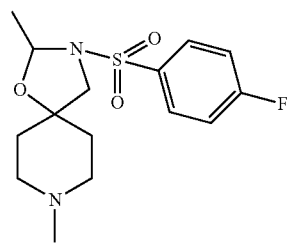 [SMILES: CC1OC2(CCN(C)CC2)CN1S(=O)(=O)c1ccc(F)cc1]

(3-(4-fluorobenzenesulfonyl)-2,8-dimethyl-1-oxa-3,8-diazaspiro[4.5]-decane), (1-(2,8-dimethyl-1-oxa-4,8-diazaspiro[4.5]dec-4-yl)-3-(1H-indol-3-yl)-propan-1-one), (1-(2,8-dimethyl-1-oxa-4,8-diaza-spiro[4.5]dec-4-yl)-2-propyl-pentan-1-one),

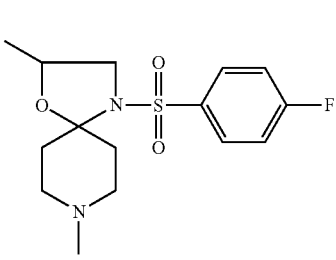 [SMILES: CC1CN(S(=O)(=O)c2ccc(F)cc2)C2(CCN(C)CC2)O1]

(4-(4-fluoro-benzenesulfonyl)-2,8-dimethyl-1-oxa-4,8-diaza-spiro[4.5]-decane),

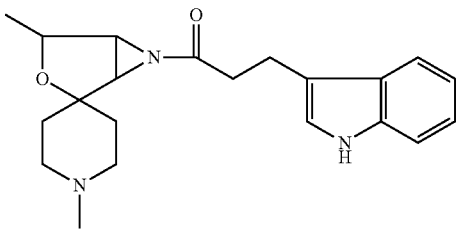 [SMILES: CC1OC2(CCN(C)CC2)C2C1N2C(=O)CCc1c[nH]c2ccccc12]

(1',4-dimethyl-6-(3-indolpropionyl)-spiro-(3-oxa-6-aza-bicyclo[3.1.0]-hexane-2,4'-piperidine)), and

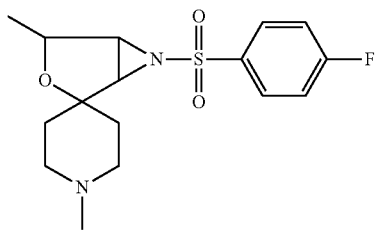 [SMILES: CC1OC2(CCN(C)CC2)C2C1N2S(=O)(=O)c1ccc(F)cc1]

(1',4-dimethyl-6-[3-(4-fluorobenzenesulfonyl)]-spiro-(3-oxa-6-aza-bicyclo[3.1.0]hexane-2,4'-piperidine)),

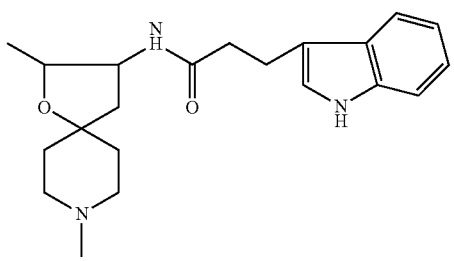 [SMILES: CC1OC2(CCN(C)CC2)CC1NC(=O)CCc1c[nH]c2ccccc12]

N-(2,8-dimethyl-1-oxa-8-aza-spiro[4.5]dec-3-yl)-3-(1H-indol-3-yl)-propionamide,

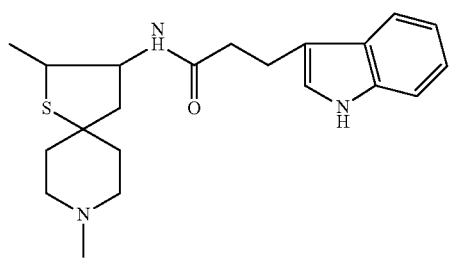 [SMILES: CC1SC2(CCN(C)CC2)CC1NC(=O)CCc1c[nH]c2ccccc12]

N-(2,8-Dimethyl-1-thia-8-aza-spiro[4.5]dec-3-yl)-3-(1H-indol-3-yl)-propionamide,

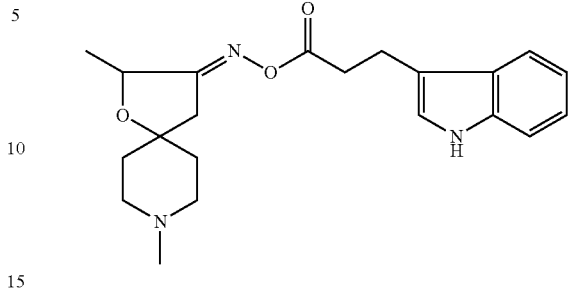

(3E)-2,8-dimethyl-1-oxa-8-azaspiro[4.5]decan-3-one-O-[3-(1H-indol-3-yl)propanoyl]oxime, or a pharmaceutically acceptable salt thereof.

15. A compound according to claim 1 which is selected from the group consisting of (1-(2,8-dimethyl-1-thia-3,8-diazaspiro[4.5]dec-3-yl)-3-(1H-indol-3-yl)propan-1-one), (+)-(1-(2,8-dimethyl-1-thia-3,8-diazaspiro[4.5]dec-3-yl)-3-(1H-indol-3-yl)propan-1-one), (−)-(1-(2,8-dimethyl-1-thia-3,8-diazaspiro[4.5]dec-3-yl)-3-(1H-indol-3-yl)propan-1-one), 1-(2,8-dimethyl-1-oxa-3,8-diazaspiro[4.5]dec-3-yl)-3-(1H-indol-3-yl)-propan-1-one, (+)-1-(2,8-dimethyl-1-oxa-3,8-diazaspiro[4.5]dec-3-yl)-3-(1H-indol-3-yl)-propan-1-one, and (−)-1-(2,8-dimethyl-1-oxa-3,8-diazaspiro[4.5]dec-3-yl)-3-(1H-indol-3-yl)-propan-1-one.

16. A pharmaceutical composition comprising a compound according to claim 1 and a pharmaceutically acceptable carrier, excipient or diluent therefor.

17. A method of treating a disease or condition which is selected from the group consisting of (i) Alzheimer's Disease, (ii) insulin resistance syndrome and (iii) type 2 diabetes comprising administering to a patient in need of such treatment an effective amount of a compound according to claim 1.

18. A compound according to claim 1 which is

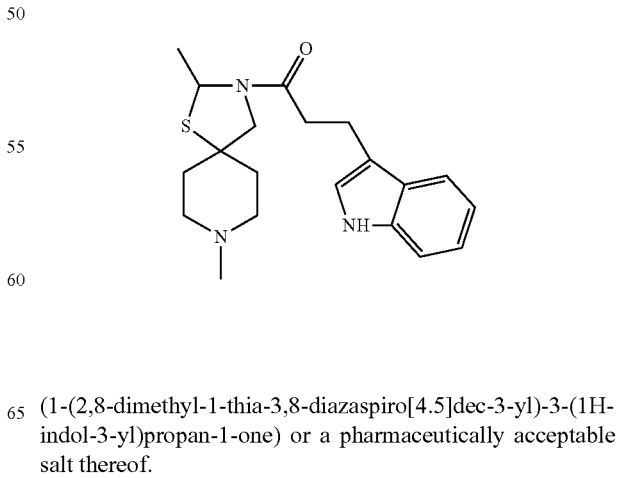

(1-(2,8-dimethyl-1-thia-3,8-diazaspiro[4.5]dec-3-yl)-3-(1H-indol-3-yl)propan-1-one) or a pharmaceutically acceptable salt thereof.

19. A compound according to claim 1 which is
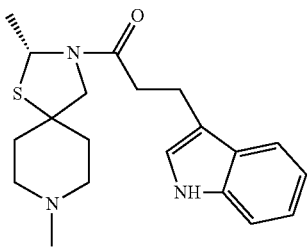 [SMILES: C[C@H]1SC2(CCN(C)CC2)CN1C(=O)CCc1c[nH]c2ccccc12]
((R)-1-(2,8-dimethyl-1-thia-3,8-diazaspiro[4.5]dec-3-yl)-3-(1H-indol-3-yl)propan-1-one) or a pharmaceutically acceptable salt thereof.
20. A compound according to claim 1 which is
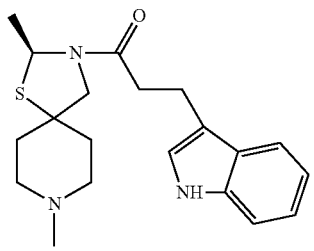 [SMILES: C[C@@H]1SC2(CCN(C)CC2)CN1C(=O)CCc1c[nH]c2ccccc12]
((S)-1-(2,8-dimethyl-1-thia-3,8-diazaspiro[4.5]dec-3-yl)-3-(1H-indol-3-yl) propan-1-one) or a pharmaceutically acceptable salt thereof.
* * * * *

UNITED STATES PATENT AND TRADEMARK OFFICE
CERTIFICATE OF CORRECTION

| | |
|---|---|
| PATENT NO. | : 8,673,931 B2 |
| APPLICATION NO. | : 13/146209 |
| DATED | : March 18, 2014 |
| INVENTOR(S) | : Fisher et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 175 days.

Signed and Sealed this
Eleventh Day of August, 2015

Michelle K. Lee
*Director of the United States Patent and Trademark Office*